US012259385B2

(12) United States Patent
Hudson et al.

(10) Patent No.: US 12,259,385 B2
(45) Date of Patent: Mar. 25, 2025

(54) SAMPLE ANALYSING DEVICE

(71) Applicant: INTELLIGENT FINGERPRINTING LIMITED, Cambridge (GB)

(72) Inventors: Mark Hudson, Norwich (GB); Jonathan Johnson, Norwich (GB); David Russell, Norwich (GB); Stephan Goetz, Stowmarket (GB); Tanya Stuchinskaya, Norwich (GB)

(73) Assignee: Intelligent Fingerprinting Limited, Cambridge (GB)

( * ) Notice: Subject to any disclaimer, the term of this patent is extended or adjusted under 35 U.S.C. 154(b) by 666 days.

(21) Appl. No.: 15/328,799

(22) PCT Filed: Jul. 24, 2015

(86) PCT No.: PCT/GB2015/052157
§ 371 (c)(1),
(2) Date: Jan. 24, 2017

(87) PCT Pub. No.: WO2016/012812
PCT Pub. Date: Jan. 28, 2016

(65) Prior Publication Data
US 2017/0307605 A1    Oct. 26, 2017

(30) Foreign Application Priority Data

Jul. 24, 2014    (GB) .................................... 1413157

(51) Int. Cl.
*G01N 33/543*    (2006.01)
*G01N 33/487*    (2006.01)
(Continued)

(52) U.S. Cl.
CPC . *G01N 33/54388* (2021.08); *G01N 33/48714* (2013.01); *G01N 33/492* (2013.01); *G01N 33/9486* (2013.01)

(58) Field of Classification Search
None
See application file for complete search history.

(56) References Cited

U.S. PATENT DOCUMENTS 4,956,275 A * 9/1990 Zuk ................. G01N 33/54386
435/25
5,851,776 A * 12/1998 Valkirs ............. G01N 33/54306
435/7.1
(Continued)

FOREIGN PATENT DOCUMENTS

CN    1135259 A    11/1996
CN    101839908 A    9/2010
(Continued)

OTHER PUBLICATIONS

DE19622503 with English Machine Translation (google translation, specification and claims), 30 pages (Year: 1997).*
(Continued)

*Primary Examiner* — Ellen J Marcsisin
(74) *Attorney, Agent, or Firm* — Lathrop GPM LLP; Brian C. Trinque; Lisbeth Robinson

(57) ABSTRACT

The present invention relates to a device and a method for analysing a sample comprising from 0.1 pg to 1 μg of analyte, and more specifically to a lateral flow device and a method for testing the presence of very low amounts of drugs or drug metabolites in a sample. The present invention also relates to a method of dissolving a bodily fluid.

19 Claims, 14 Drawing Sheets

Figure 1:
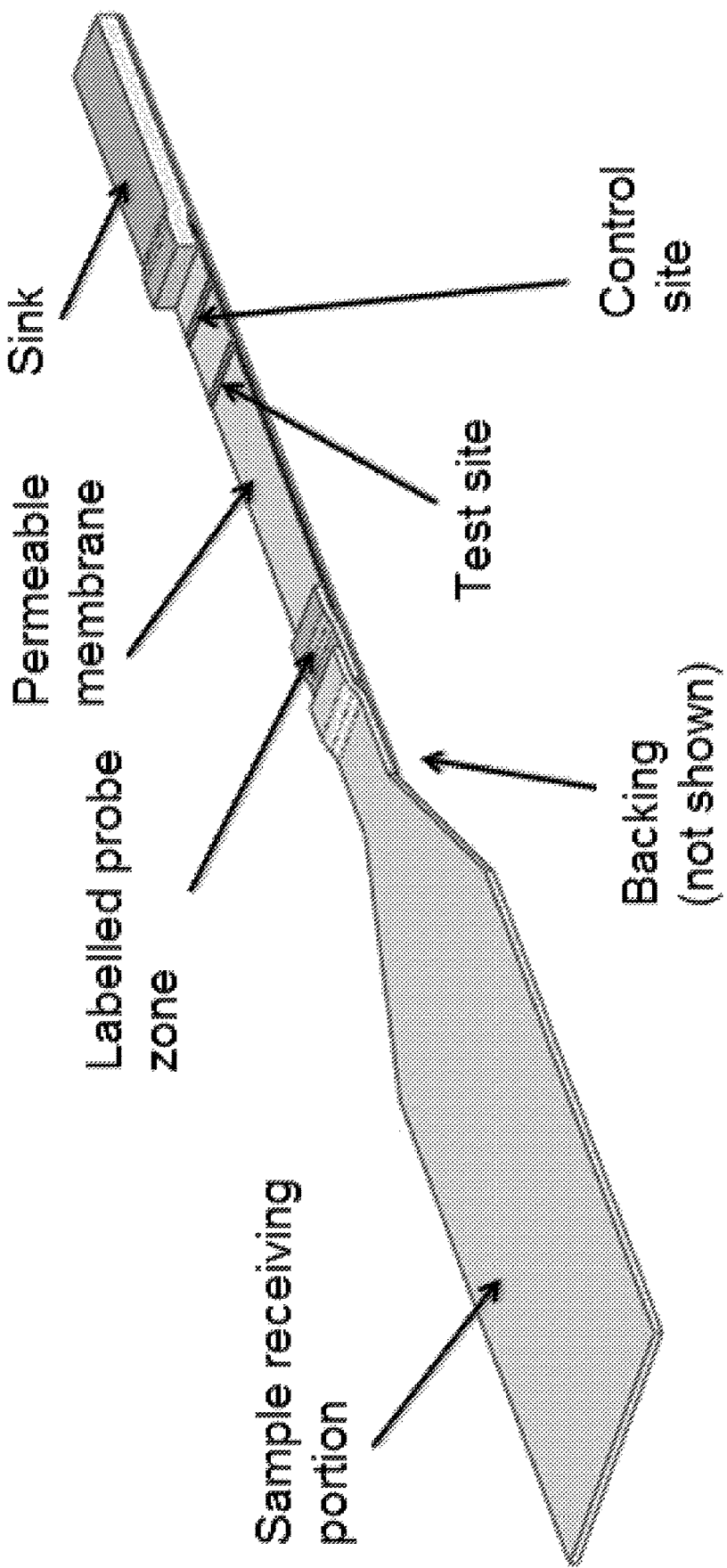

(51) Int. Cl.
*G01N 33/49* (2006.01)
*G01N 33/94* (2006.01)

(56) References Cited

U.S. PATENT DOCUMENTS

| | | | | |
|---|---|---|---|---|
| 5,922,533 | A * | 7/1999 | Vallari | G01N 33/54386 422/561 |
| 2001/0034068 | A1* | 10/2001 | Spivey | G01N 33/54366 436/518 |
| 2004/0082077 | A1 | 4/2004 | Hu | |
| 2008/0194041 | A1* | 8/2008 | Guirguis | A61B 10/0051 436/165 |
| 2008/0241958 | A1* | 10/2008 | Yee | G01N 33/76 436/501 |
| 2009/0197283 | A1* | 8/2009 | Gold | B01L 3/5029 435/7.9 |
| 2012/0075626 | A1* | 3/2012 | Geva | B01L 3/5023 356/244 |
| 2012/0165626 | A1* | 6/2012 | Irina | A61B 10/0064 600/316 |
| 2013/0102003 | A1* | 4/2013 | Gibbs | G01N 33/558 435/6.11 |
| 2014/0093865 | A1* | 4/2014 | Espinosa | G01N 33/558 435/5 |
| 2014/0370616 | A1* | 12/2014 | Gupta | G01N 33/82 436/501 |

FOREIGN PATENT DOCUMENTS

| | | | | |
|---|---|---|---|---|
| CN | 102305854 A | 1/2012 | | |
| CN | 103536296 A | 1/2014 | | |
| GB | 2520063 A | 5/2015 | | |
| WO | 03008933 A2 | 1/2003 | | |
| WO | 2010025190 A1 | 3/2010 | | |
| WO | 2011008581 A2 | 1/2011 | | |
| WO | WO-2012129650 A1 * | 10/2012 | | G01N 33/82 |
| WO | WO-2014137860 A2 * | 9/2014 | | G01N 33/54346 |

OTHER PUBLICATIONS

Sussman, "Fingertip diagnosis: can fingerprints do more than just solve crimes", CNN. Jul. 2007 (Year: 2007).*
National Institute on Drug Abuse (NIDA), Commonly Abused Prescription drugs, (2011), 2 pages, online available at: https://www.drugabuse.gov/sites/default/files/rx_drugs_placemat_508c_10052011.pdf, Accessed: May 25, 2021 (Year: 2011).*
Wikipedia contributors. (Jan. 12, 2023). Drop (unit). In Wikipedia, The Free Encyclopedia. Retrieved 14:25, Mar. 29, 2023, from https://en.wikipedia.org/w/index.php?title=Drop_(unit)&oldid=1133079330 (Year: 2023).*

* cited by examiner

Fingerprint Collection Pad Material: Ahlstrom Grade 1281

Donor: 04745008
>1700ng/ml MOR

Donor: 04745009
>10 ng/ml MOR

Donor: 04745007
Negative for MOR 5s exposure time

*40ug/ml BSA-Morphine stock (test line 0.25μl/cm deposition)*
*50ng labelled antibody in conjugate pad*

0pg     150pg     300pg     450pg

For detection around the opiate Cut-off

*40ug/ml BSA-Morphine stock (test line 0.25μl/cm deposition)*
*100ng labelled antibody in conjugate pad*

0pg     150pg     300pg     450pg

Decreased sensitivity for higher gross detection

*80ug/ml BSA-Morphine stock (test line 0.25μl/cm deposition)*
50ng antibody in conjugate pad 0pg    150pg    300pg    450pg

*80ug/ml BSA-Morphine stock (test line 0.25μl/cm deposition)*
100ng antibody in conjugate pad 0pg    150pg    300pg    450pg

SAMPLE ANALYSING DEVICE

CROSS-REFERENCE TO RELATED APPLICATIONS

This application is a U.S. national phase application and claims the benefit of priority under 35 U.S.C. § 371 of PCT/GB2015/052157, titled "SAMPLE ANALYSING DEVICE" and filed on Jul. 24, 2015, the contents of which are hereby incorporated herein by reference in their entireties for all purposes, and which in turn claims priority to GB1413157.7 filed on Jul. 24, 2014.

The present invention relates to a device and a method for analysing a sample comprising from 0.1 pg to 1 µg of analyte, and more specifically to a lateral flow device and a method for testing the presence of very low amounts of drugs or drug metabolites in a sample. The present invention also relates to a method of dissolving a bodily fluid.

BACKGROUND TO THE INVENTION

Doctors, health-care workers, rehab clinics, coroners, employers, government agencies, sports groups, the police and the public in general are interested in the presence and levels of various substances in bodily fluids including blood, urine, saliva and sweat. Among the substances which have been measured in clinical analysis for a long time are glucose, cholesterol, various enzymes such as amylase and creatine kinase, and drugs and their metabolites.

Lateral flow testing devices are widely used for the detection of specific compounds, or analytes, in a biological fluid specimen. One or more reagents are positioned on a solid material, such as a cellulose or paper strip, the reagents being selected as necessary or helpful in detection of the analyte in question. A fluid sample is deposited onto the strip and will migrate, by capillary action, along the strip where the chemical reactions may take place, depending on the presence or absence of the analyte, in situ.

Devices for testing for the presence of substances of abuse, for example, drugs regulated by law with respect to possession and use, by chemical analysis of a biological fluid sample are well known. In the past, for example, methamphetamines have been detected using a number of techniques, including thin layer chromatography (TLC), gas chromatography (GC), and high performance liquid chromatography (HPLC). These methods generally involve chemical extractions of the drugs, complicated procedures requiring highly trained personnel and lengthy assay times. Thin layer chromatography is labour intensive and lacks sensitivity. Gas chromatography and high performance liquid chromatography, each of which is also labour intensive, require highly trained personnel to carry out extractions of the analyte from the biological matrix. In addition, gas chromatography normally requires a derivation step.

More recently, competitive binding immunoassays have been developed for testing a biological fluid for the presence of certain substances of abuse, and these provide a preferable alternative to the physical methods described briefly hereinabove. Immunoassay test devices generally include an absorbent, fibrous strip having one or more reagents incorporated at specific zones on the strip. The fluid sample is deposited onto the strip and by capillary action the sample will migrate along the strip, entering specific reagent zones in which a chemical reaction may take place. At least one reagent is included which manifests a detectable response, for example a colour change, in the presence of a certain amount of the substance of interest.

One limitation with known lateral flow "drugs of abuse" testing devices and methods based on immunoassay technologies is that the devices are not sensitive enough to qualitatively and/or quantitatively detect low amounts of the analyte(s) in question in a reliable manner. Such a limitation means that biological samples must generally be provided to known devices in large amounts and/or with a high concentration of analyte, for example in the form of blood or urine.

It is one object of the present invention to overcome at least some of the disadvantages of the prior art or to provide a commercially useful alternative thereto.

It is a further object of the present invention to provide an easy-to-use, inexpensive device and method having increased sensitivity to an analyte(s) in a sample without the need for more complicated, costly confirmation procedures.

It is a further object of the present invention to provide a more reliable device and method for qualitatively and/or quantitatively analysing a sample comprising a low amount of analyte(s).

It is a further object of the present invention to provide a method of dissolving a bodily fluid for use in the device and method of analysing a sample.

SUMMARY OF THE INVENTION

In a first aspect the present invention provides a lateral flow device for analysing a sample comprising from 0.1 pg to 1 µg of analyte, the device comprising:
  a sample receiving portion;
  a probe zone downstream of the sample receiving portion, the probe zone comprising a labelled probe capable of binding to the analyte; and
  a test site, downstream of the probe zone, the test site comprising a first immobilised capture reagent capable of binding to the labelled probe;
  the device being configured to permit movement of a buffer from the sample receiving portion to the probe zone and from the probe zone to the test site.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

In a further aspect the present invention provides a method for analysing a sample comprising from 0.1 pg to 1 µg of analyte, the method comprising:
  (a) providing a sample, the sample containing or not containing from 0.1 pg to 1 µg of an analyte of interest;
  (b) dissolving at least a portion of the sample in a buffer to form a dissolved sample solution;
  (c) contacting at least a portion of the dissolved sample solution with a probe zone comprising a labelled probe to dissolve at least a portion of the labelled probe and allow the labelled probe to bind with the analyte, where present, in the portion of the dissolved sample solution to form a labelled probe-analyte complex;
  (d) passing the labelled probe and/or labelled probe complex through a test site comprising a first immobilised capture reagent capable of binding to the labelled probe;
  (e) determining whether or not the amount of analyte, if any, in the sample exceeds a threshold value by detecting the amount of labelled probe in the test site.

In a further aspect the present invention provides a method of preparing the lateral flow device described herein, comprising:

providing a fingerprint receiving portion to a substrate;
applying a labelled probe to the substrate to create a probe zone;
applying to the substrate and immobilising thereon a first capture reagent capable of binding to the labelled probe to create a test site.

In a further aspect the present invention provides a kit for the analysis of a sample, comprising:
the device described herein; and
a fluorescence, ultraviolet, infrared and/or a far infrared detector.

In a further aspect the present invention provides a method of dissolving a bodily fluid, the method comprising contacting a bodily fluid with a buffer, the buffer comprising:
a water miscible organic solvent;
a surfactant, preferably a detergent; and
a buffering agent.

In a further aspect the present invention provides a lateral flow device for detecting from 0.1 pg to 1 µg of analyte in a sample.

Other preferred embodiments of the device and methods according to the invention appear throughout the specification and in particular in the examples.

The present inventors have surprisingly found that the lateral flow device and the method of the present invention are able to reliably detect whether or not low amounts, for example from 0.1 pg to 1 µg, of analyte are present in a sample. If the analyte is present, the device and method can also provide precise information regarding the identity and amount of analyte present in the sample.

Without wishing to be bound by theory, it is thought that the device and method described herein are able to detect and quantify low amounts of analyte in samples having low volumes. For example, the sample may be a substantially dry sample, such that the sample, when deposited, comprises insufficient liquid to move by capillary action through a substrate without being dissolved in a set volume of buffer.

The present inventors have now surprisingly found that, when a very low volume/mass of a substantially dry sample is deposited over a large surface area, low amounts of analyte in the sample are able to be detected by using a buffer to rapidly release the analyte (e.g. a drug or drug metabolite) from the sample (e.g. a fingerprint). As the buffer passes through the sample, the analyte molecules concentrate at the buffer solvent front, where they are then brought into contact with labelled probes (e.g. labelled antibodies) specific to the analyte.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

Lateral flow immunoassays are simple tests for rapid detection of the presence or absence of a target analyte in a sample for home testing, point of care testing, or laboratory applications. Lateral flow devices preferably utilise a solid support through which a mobile phase (e.g., a buffer) can flow through by capillary action to a reaction matrix where a detectable signal, such as colour changes or colour differences at a test site, may be generated to indicate the presence or absence of the target analyte. As used herein, the term "capillary action" refers to the process by which a molecule is drawn across the lateral test device due to such properties as surface tension and attraction between molecules.

The lateral flow device as described herein is for use in an immunoassay i.e. a method for analysing a sample comprising from 0.1 pg to 1 µg of analyte. The immunoassay comprises a competitive binding assay, where any labelled probe (e.g. antibody) not bound to analyte provides an identifiable signal in the test site whilst any labelled probe bound to analyte, e.g. in the form of an immunocomplex, passes through the test site and does not provide an identifiable signal in the test site. As the number of analyte molecules present in the sample increases, the amount of unbound labelled probe passing through the test site decreases. Thus the higher the level of analyte in the sample, the weaker the identifiable signal at the test site will be. Such a device/method allows qualitative tests to be undertaken, i.e. whether or not the sample contains an analyte of interest. Such a device/method also allows quantitative tests to be undertaken by measuring the intensity of the signal at the test site. The higher the intensity of the signal, the lower the amount of analyte in the sample.

In a first embodiment, the present invention provides a lateral flow device for analysing a sample comprising from 0.1 pg to 1 µg of analyte, the device comprising:
a sample receiving portion;
a probe zone downstream of the sample receiving portion, the probe zone comprising a labelled probe capable of binding to the analyte; and
a test site, downstream of the probe zone, the test site comprising a first immobilised capture reagent capable of binding to the labelled probe;
the device being configured to permit movement of a buffer from the sample receiving portion to the probe zone and from the probe zone to the test site.

In use, the labelled probe will bind to the immobilised first capture reagent in the test site, unless it is blocked by analyte present in the sample.

As used herein, the term "sample" refers to a fluid sample which may or may not contain one or more analytes of interest. A sample may comprise a liquid body fluid (for example, urine, blood, plasma, serum, sweat, saliva, ocular fluid, spinal fluid, and the like) from humans or animals.

Preferably, the device is for analysing a sweat sample, preferably an eccrine sweat sample. More preferably, the device is for analysing a finger-sweat and/or palm-sweat and/or toe-sweat sample. Most preferably, the device is for analysing a finger-sweat sample. The term "finger-sweat" refers to sweat secreted by sweat glands in the skin of fingers of mammals, including humans. Finger-sweat includes sweat deposited as an impression of a finger's ridge pattern, i.e. a latent fingerprint. The term "palm-sweat" refers to sweat secreted by sweat glands in the skin of palms of mammals, including humans. The term "toe-sweat" refers to sweat secreted by sweat glands in the skin of toes of mammals, including humans. Toe-sweat includes sweat deposited as an impression of a toe's ridge pattern, i.e. a latent toe-print.

Preferably, the device is for analysing a sample comprising from 0.1 pg to 1 µg, or from 0.1 pg to 500 ng, or from 0.1 pg to 200 ng, or from 0.1 pg to 100 ng, or from 0.1 pg to 50 ng, or from 0.1 pg to 10 ng, or from 0.1 pg to 5 ng of analyte. More preferably, the device is for analysing a sample comprising from 0.5 pg to 4 ng, or from 0.5 pg to 3 ng, or from 1 pg to 2 ng, or from 1 pg to 1 ng, or from 1 pg to 500 pg, or from 1 pg to 400 pg, or from 1 pg to 300 pg, or from 2 pg to 250 pg, or from 3 pg to 225 pg, or from 5 pg to 200 pg of analyte.

Preferably, the analyte comprises a drug metabolite and/or a drug.

The sample receiving portion is for receiving the sample, and may be comprised, for example, of a fibrous material which preferably absorbs the sample. Preferably, the sample receiving portion is located on a permeable membrane which comprises one or more of cotton, glass fibre, rayon, polyester, nylon, cellulose, nitrocellulose and spun polyethylene. More preferably, the sample receiving portion is located on a permeable membrane comprising Fusion 5, available from GE Healthcare. Fusion 5 is advantageous because it allows the sample on the sample receiving portion to be visualised, for example with a camera, and/or recorded, thereby increasing the accuracy and reliability of any tests undertaken using the device. In particular, visualisation may be useful because the analyser can confirm whether or not the sample receiving portion has received a sample, for example a fingerprint.

Preferably, the sample receiving portion comprises one or more indentations and/or lines configured to concentrate and/or guide the sample downstream to the probe zone. Indentations and/or lines on the sample receiving portion may increase the speed of flow of the buffer downstream towards the probe zone and partition the sample receiving portion into separate channels. In one embodiment, the lines comprise hydrophobic ink.

Preferably, the sample receiving portion is configured to receive the fingerprint of an average adult human. Preferably, the sample receiving portion has an area of 100 $mm^2$ to 400 $mm^2$, or from 200 $mm^2$ to 350 $mm^2$, or from 250 $mm^2$ to 350 $mm^2$. More preferably, the sample receiving portion has an area of 275 $mm^2$ to 325 $mm^2$. Alternatively, preferably, the sample receiving portion is configured to receive the fingerprint of a neonate, the sample receiving portion preferably having an area of 25 $mm^2$ to 75 $mm^2$, or from 30 $mm^2$ to 60 $mm^2$. Preferably, the sample receiving portion is substantially oblong, substantially circular or substantially oval. Preferably, the sample receiving portion is configured such that the area of the sample received by one person, for example in the form of a fingerprint, is substantially the same as the area of the sample received by another person of similar age. Such a configuration of sample receiving portion provides better normalised results from sample to sample.

Preferably, the device further comprises a buffer receiving portion upstream of the sample receiving portion, the device being configured to permit movement of a buffer from the buffer receiving portion to the sample receiving portion.

Preferably, the device further comprises a reservoir for holding a buffer, the device being configured such that, in use, the movement of a buffer from the reservoir to the buffer receiving portion is permitted.

Preferably, the reservoir has a volume of from 100 to 500 µl. More preferably, the reservoir has a volume of from 100 to 450 µl, or from 100 to 400 µl, or from 100 to 350 µl, or from 100 to 300 µl, or from 100 to 250 µl, or from 100 to 200 µl. Alternatively, preferably, the reservoir has a volume of from 125 to 300 µl, or from 150 to 250 µl, or from 175 to 215 µl. Alternatively, preferably, the reservoir has a volume of from 150 to 550 µl, or from 200 to 500 µl, more preferably from 250 to 400 µl, or from 300 to 375 µl, most preferably from 325 to 350 µl.

Preferably, the reservoir contains from 100 to 500 µl of buffer. More preferably, the reservoir contains from 100 to 450 µl, or from 100 to 400 µl, or from 100 to 350 µl, or from 100 to 300 µl, or from 100 to 250 µl, or from 100 to 200 µl of buffer. Alternatively, preferably, the reservoir contains from 125 to 300 µl, or from 150 to 250 µl, or from 175 to 215 µl of buffer. Alternatively, preferably, the reservoir contains from 150 to 550 µl, or from 200 to 500 µl of buffer. More preferably, the reservoir contains from 250 to 400 µl of buffer, or from 300 to 375 µl, most preferably from 325 to 350 µl of buffer.

Preferably, the reservoir is a buffer blister. The term "buffer blister" refers to a sealed reservoir containing a volume of buffer, at least a portion of which is released on opening the blister, for example by piercing (a wall of) the blister. Buffer blisters are advantageous because the buffer therein may, for example, be kept sterile until the moment of release. Buffer blisters are also advantageous because it is easy to observe that the blister is opened/broken, thus reducing the risk of the buffer therein being tampered with before use.

Preferably, the buffer comprises a water miscible organic solvent, a surfactant, preferably a detergent, and a buffering agent. It is advantageous that the buffer comprises all of the three components mentioned above. In particular, the buffer as described herein preferably flows in a polarised manner downstream through the device at a controlled flow rate by capillary action, meaning that the flow rate is consistent and predictable from the moment of being received at the sample receiving portion. The buffer is also preferably effective at solubilising the analyte at the solvent front, thereby presenting the analyte to the antibody in a concentrated, efficient and reproducible way. The buffer's individual components and preferred amounts thereof are described in further detail below.

Water miscible solvents are known in the art. Preferably, the water miscible organic solvent comprises one or more of ethanol, methanol and tetrahydrofuran. Preferably, the buffer comprises 10 to 30 v/v % water miscible organic solvent. More preferably, the buffer comprises from 15 to 25 v/v %, or from 18 to 22 v/v % water miscible organic solvent. The water miscible organic solvent helps hydrophilic and hydrophobic molecules partition in water.

Surfactants are known in the art and may include any molecule that forms micelles, for example amphiphilic molecules. Preferably, the surfactant comprises one or more of TWEEN-20, TWEEN-80, TRITON X-100, tetraoctyl ammonium bromide, Polyethylene glycol (PEG) and octanoic acid. Alternatively, preferably, the surfactant comprises one or more of TWEEN-20, TWEEN 80, TRITON X-100, TRITON X-114, tetraoctyl ammonium bromide, Polyethylene glycol (PEG) and octanoic acid. More preferably, the surfactant comprises one or more of TWEEN-20, TWEEN 80, TRITON X-100 and tetraoctyl ammonium bromide. Alternatively, more preferably, the surfactant comprises one or more of TWEEN-20, TWEEN 80, TRITON X-100, TRITON X-114 and tetraoctyl ammonium bromide. Preferably, the buffer comprises 0.1 to 0.15 w/v % surfactant. More preferably, the buffer comprises 0.11 to 0.14 w/v %, or 0.12 to 0.13 w/v % surfactant. The surfactant, preferably a detergent, is thought to aid release of analyte, e.g. drugs and/or drug metabolites, from the bodily fluid. The surfactant molecules are preferably present in a concentration above their critical micelle concentration (CMC). The micelles thus present within the surfactant are preferably able to act as a carrier for any hydrophobic analyte, e.g. drugs and drug metabolites, and allow presentation of said analyte during analysis undertaken on the bodily fluid.

Suitable buffering agents are known in the art. Preferably, the buffering agent comprises one or more of HEPES, Tris, TRIZMA and phosphate buffer. Preferably, the buffer comprises 5 to 100 mM buffering agent. More preferably, the buffer comprises 5 to 75 mM, or 5 to 50 mM, or 5 to 25 mM, or 5 to 15 mM, or 5 to 10 mM, or 6 to 9 mM, or 7 to 8 mM buffering agent. The buffering agent is thought to assist in increasing the solubility of the analyte, e.g. drugs and/or drug metabolites, based on their pKa and PI values.

Preferably, the buffer further comprises a salt. Preferably, the salt is selected from NaCl, KCl or a mixture thereof. It is thought that when the buffer further comprises a salt, the stringency of the test is improved, for example, an increased level of salt in the buffer may help to reduce the intensity of background noise when analysing the test site(s) and/or the control site and/or the normalisation site.

Preferably, the buffer further comprises one or more anti-oxidants. Suitable anti-oxidants include ethyl acetate, methyl anthranilate, 2-pentyl butyrate and ethyl butyrate. Anti-oxidants may help to prevent the oxidation of the analyte or metabolite thereof and any organic material in the sample, such as fingerprint lipids. This is desirable because, if the analyte and/or metabolite thereof is oxidised, its properties (e.g. its charge) may change. Any changes in physical or chemical properties could interfere with the analyte's or metabolite's ability to bind with the probe (e.g. an antibody) and therefore such changes are preferably avoided by the presence of one or more anti-oxidants in the buffer.

Preferably, the buffer further comprises an emulsifier. Preferably, the emulsifier is selected from deoxycholate, cholesterol and combinations thereof. More preferably, the emulsifier is deoxycholate. Without wishing to be bound by theory, an emulsifier such as deoxycholate helps to present any analyte or metabolites thereof in the sample to the probe. This is thought to be achieved by the emulsifier aiding presentation of any hydrophobic analyte or metabolite to the labelled probe.

Downstream of the sample receiving portion is the probe zone. Preferably, in use, the buffer (comprising the dissolvable elements, e.g. analyte, from the sample) is drawn into and through the labelled probe zone, which releases a labelled probe into the buffer. The labelled probe is preferably located on a permeable membrane, wherein the permeable membrane may comprise one or more of nitrocellulose, polyester, rayon and glass fibres. Preferably, the permeable membrane comprises Ahlstrom ReliaFlow™ 800. Alternatively, preferably, the permeable membrane comprises Fusion 5, available from GE Healthcare.

The permeable membrane on which the sample receiving zone and/or the probe zone and/or the test site are preferably located may be the same membrane or separate respective membrane. The membrane at the sample receiving portion may comprise a different material to the material at the probe zone/test site. Alternatively, the material may be the same at the sample receiving portion, the probe zone and the test site.

Preferably, the permeable membrane is configured to permit controlled movement of buffer. Preferably the membrane is permeable in that it allows a reagent (e.g. a buffer) comprising analyte (e.g. a drug molecule or drug metabolite) to pass through the membrane by capillary action. Preferably, the permeable membrane comprises nitrocellulose or a similar blotting material. Preferably the membrane does not allow chromatography effects, i.e. the membrane preferably does not allow the labelled probe to migrate slower or faster than the analyte such that the labelled probe and analyte separate or do not bind efficiently. In use, a membrane which is configured to allow controlled and predictable movement of buffer increases the accuracy and reliability of the assay and allows results to be reproduced and normalised between samples.

In one preferable embodiment, the permeable membrane is treated with hydrophobic glue which provides pores through which a buffer may flow in a pore size dependent manner. Alternatively, or additionally, the permeable membrane comprises a plurality of layers, wherein the layers are optionally separated by a porous glue, which is thought to regulate the flow of buffer from e.g. the buffer receiving portion to the sample receiving portion, thereby giving a desirable rate of flow, the rate maximising the solubilisation of analyte from the sample which is then concentrated at the solvent front.

As used herein, the term "probe" refers to one or more molecules containing one or more variable analyte binding domain(s). The probe is specific to an analyte (e.g. the drug or drug metabolite which may be present in the sample) and capable of binding to the analyte to form a probe-analyte complex (e.g. an immunocomplex). As used herein, the term "probe specific to" refers to a probe which does not bind significantly to any sample components other than the analyte of interest. As used herein, the term "binding" refers to an interaction or complexation between a probe and an analyte, resulting in a sufficiently stable complex.

Preferably, the probe is selected from the group consisting of antibodies, aptamers, and mixtures thereof. Alternatively, preferably, the probe is selected from the group consisting of antibodies, aptamers (or other DNA based protein-binding structures), affimers (or other aminoacid based protein-binding structures), and mixtures thereof. More preferably the probe is an antibody. The term "antibody" includes natural and artificial antibodies as well as divalent antibodies and monovalent antibody Fab and $F(ab')_2$ fragments. Antibodies bind by means of specific binding sites to specific antigenic determinants or epitopes on antigens, e.g. drugs or drug metabolites. Preferably, when the probe is an antibody and the analyte is an antigen of interest, the antibody is specific to the antigen (e.g. the drug or drug metabolite which may be present in the sample) and capable of binding to the antigen to form an immunocomplex (an antibody-antigen complex). As used herein, the term "antibody specific to" refers to an antibody which does not bind significantly to any sample components other than the antigen of interest.

Preferably, the labelled probe comprises two or more different antibodies. In particular, one antibody may be capable of binding to one antigen and a different antibody may be capable of binding to a different antigen. For example, one antibody may be an antibody capable of binding to morphine and/or a metabolite thereof and another antibody may be an antibody capable of binding to cocaine and/or a metabolite thereof. Providing two or more different antibody is therefore advantageous because more than one analyte, e.g. a drug or drug metabolite, can be detected in the sample, if present. When the labelled probe comprises two or more different antibodies, the different antibodies are labelled with different labels or the same label. Different labels allow the identification and/or quantification of different analytes in the sample, e.g. different drugs and/or their metabolites in the same test site, thereby improving the multiplex capability of the device. When the different antibodies are labelled with the same label, different test sites are used to identify and/or quantify the different analytes in the sample, e.g. different drugs and/or their metabolites.

Preferably, the probe comprises divalent antibodies and/or monovalent antibody Fab and F(ab')$_2$ fragments. A "divalent antibody" is an antibody having two binding sites. A divalent antibody is therefore capable of binding to two molecules of an antigen, e.g. a drug and/or a drug metabolite. A "monovalent antibody Fab and F(ab')$_2$ fragments" is an antibody fragment having one binding site. A monovalent antibody Fab or F(ab')$_2$ fragment is therefore thought to be capable of binding to one molecule of an antigen, e.g. a drug and/or a drug metabolite, leading to increased sensitivity of the device.

Alternatively, preferably, the probe comprises one or more affimers. Methods of preparing affimers specific to particular targets are known in the art. For example, phage display libraries of potential targets, e.g. drugs of abuse, metabolites thereof, or associated ligands, may be generated through in vitro technologies. Affimers may then be generated to display a high affinity binding surface for the specific targets.

In particular, in vitro display technologies permits the use of defined selection conditions and provides immediate availability of the sequence encoding the antibody. The amenability of in vitro display to high-throughput applications may broaden the prospects for their wider use in basic and applied research. Display libraries can contain up to $2.5 \times 10^{11}$ members generated from the human repertoire. In vitro display technologies therefore offer opportunities to select and characterise those display members which are specific for drugs of abuse and/or metabolites thereof.

The probe is conjugated to a detectable label which provides a means of visualising or detecting the probe, and may comprise a chromogen, a catalyst, a fluorescent compound, a chemiluminescent compound, a colloidal gold, a dye particle, a quantum dot, or a latex particle tagged with a detector reagent such as, for example, a coloured or fluorescent dye. Preferably, the labelled probe is detectable in radiation having a wavelength of 400 nm to 1 mm. More preferably, the labelled probe is detectable in radiation having a wavelength of 400 nm to 500 µm, or from 400 nm to 100 µm, or from 400 nm to 10 µm, or from 400 nm to 1 µm, or from 400 nm to 800 nm, or from 450 nm to 700 nm. Preferably, the labelled probe comprises a fluorescently labelled probe. Alternatively, preferably, the labelled probe comprises a one or more quantum dots.

Preferably, the probe zone comprises from 10 pg to 1 µg of a labelled probe. More preferably, the probe zone comprises from 10 pg to 500 ng of a labelled probe. More preferably still, the probe zone comprises from 10 pg to 400 ng, or from 10 pg to 300 ng, or from 10 pg to 250 ng, or from 10 pg to 200 ng, or from 10 pg to 100 ng, or from 10 pg to 1 ng, or from 10 pg to 500 pg, or from 10 pg to 200 pg, of a labelled probe. Alternatively, preferably, the probe zone comprises from 50 pg to 500 ng, or from 200 pg to 400 ng, or from 500 pg to 300 ng, or from 1 ng to 250 ng, or from 10 ng to 200 ng, or from 20 ng to 150 ng, or from 30 ng to 100 ng of a labelled probe.

Providing a small amount, such as from 10 pg to 100 ng, or from 10 pg to 1 ng, or from 10 pg to 500 pg, or from 10 pg to 200 pg, of labelled probe is thought to increase the sensitivity of the assay, and very small levels of analyte, e.g. drug/drug metabolite, from the sample can be accurately detected. Providing a larger amount, such as 200 ng to 1 µg, of a labelled probe allows the detection and quantification of higher levels of analyte in the sample, which may be useful for gross detection levels to identify when a substance, e.g. a drug, has killed someone. It is understood that the amount of labelled probe at the labelled probe zone will vary depending on the affinity of the probe to the analyte. For example, different antibodies may have different affinities, so more or less antibody may be required to provide the optimum levels of sensitivity. For example, mouse antibodies typically have a $K_D$ value of around $10^{-9}$M while rabbit antibodies typically have a $K_D$ value of around $10^{-11}$M, so the rabbit antibodies have a greater average binding affinity, typically 1 to 2 orders more. It is emphasised that these example values are average $K_D$ values around which there is a normal Gaussian distribution, so some (a small amount) of mouse antibodies will perform as well as rabbit antibodies and vice versa.

Preferably, the width of the device (for example the width of the substrate or permeable membrane) at the sample receiving portion is greater than at the probe zone. This is advantageous because, in use, the buffer may pass through a greater area of the sample receiving portion thereby dissolving a larger portion/the entirety of the analyte at the solvent front. The narrowing of the device at or upstream of the probe zone preferably ensures that the analyte is then further concentrated at the buffer's solvent front when it is presented at the probe zone as a minimal volume of concentrated solute, where the binding of any analyte with the labelled probe takes place. Presenting the highest concentration of analyte at the buffer's solvent front to the labelled probe improves the kinetics of the two entities binding to each other and thereby increases the efficiency, sensitivity and reliability of the assay.

Alternatively, preferably, the width of the device at the sample receiving portion and at the probe zone is substantially the same. This may be advantageous and convenient in the manufacture and packaging of the devices because the devices may be bulk-produced more quickly and easily. Wastage may also be reduced due the shape of the devices (e.g. the substrate or membrane) which may tessellate and, for example, two or more substantially rectangular devices or membranes may be produced from one piece of rectangular starting material with no or minimal wastage.

Downstream of the probe zone is the test site, the test site comprising a first immobilised capture reagent capable of binding to the labelled probe. The test site is preferably located on a permeable membrane, preferably a nitrocellulose permeable membrane.

The test site comprises a first capture reagent which has been immobilised in a particular area of the device, preferably on the permeable membrane, to "capture" or bind a specific molecule. As used herein, the term "first immobilised capture reagent" means that the first capture reagent is attached to or confined within the test site such that lateral flow of fluids across the test site during an assay will not dislodge the first capture reagent. Accordingly, any labelled probe which is not part of a labelled probe-analyte complex (e.g. an immunocomplex) has capacity to bind to the first immobilised capture reagent.

Preferably, the first immobilised capture reagent comprises an antigen capable of binding to the labelled probe. Preferably the antigen is a drug and/or drug metabolite that may also be present as analyte in the sample. Preferably, the labelled probe is an antibody and the antigen is a drug and/or drug metabolite that may also be present as analyte in the sample. Alternatively, preferably, the labelled probe is an affimer and the antigen is a drug and/or drug metabolite that may also be present as analyte in the sample.

Preferably, the test site comprises from 1 ng to 500 ng of the first immobilised capture reagent. More preferably, the test site comprises from 1 ng to 400 ng, or from 1 ng to 350 ng, or from 1 ng to 300 ng, or from 1 ng to 250 ng, or from 5 ng to 225 ng, or from 10 ng to 200 ng of the first immobilised capture reagent. Providing a small amount, such as from 1 ng to 300 ng, or from 1 ng to 250 ng, or from 1 ng to 250 ng, of first immobilised capture reagent is thought to increase the sensitivity of the assay, and very small levels of analyte, e.g. antigen, from the sample can be accurately detected. Providing a larger amount, such as 350 ng to 500 ng, of first immobilised capture reagent allows the detection of higher levels of analyte in the sample, which may be useful for gross detection levels to identify when a substance, e.g. a drug, has killed someone.

In one embodiment, the first immobilised capture reagent comprises two or more different antigens capable of binding to the labelled probe. In particular, when the labelled probe comprises two or more different antibodies, one antigen may be capable of binding to one antibody and a different antigen may be capable of binding to a different antibody. For example, one antigen may be cocaine or a metabolite thereof and another antigen may be morphine or a metabolite thereof.

Preferably, the device comprises a plurality of test sites. Preferably, each test site comprises a different first immobilised capture reagent, for example, different immobilised antigens, capable of binding to the labelled probe. In particular, when the labelled probe comprises two or more different antibodies, one antigen capable of binding to one antibody may be immobilised at a first test site, and a different antigen capable of binding to a different antibody may be immobilised at a second test site.

Preferably, the test sites are arranged in series. Alternatively, preferably, the test sites are arranged in parallel.

Preferably, the first capture reagent is immobilised at the test site by conjugation to a linker molecule. The linker molecule-first capture reagent conjugate is immobilised at the test site. Preferably, the linker molecule-first capture reagent conjugate is immobilised at the test site by hydrophobic and/or electrostatic interaction. The linker molecule is preferably selected from the group consisting of a protein, a synthetic polymer, a modified sugar molecule, modified DNA and mixtures of two or more thereof. Preferably, the linker molecule is a protein, which may be a large peptide molecule. More preferably, the protein comprises Keyhole Limpet Hemacyanin (KLH), Bovine Serum Albumin (BSA), Human Serum Albumin (HSA), Bovine Thyroglobulin (BTG), Horse Radish Peroxidase (HRP), or mixtures of one or more thereof. Most preferably, the protein comprises Bovine Serum Albumin (BSA). The linker molecule prevents migration of the first capture reagent from the test site.

When the first capture reagent is immobilised via conjugation to an immobilised protein, preferably, each immobilised protein molecule is conjugated to 10 to 50, or 15 to 40, or 20 to 35 molecules of first capture reagent. For example, when the protein is BSA and the first capture reagent is morphine, each BSA molecule immobilised at the test site is conjugated to around 30 morphine molecules.

Preferably, the linker molecule is provided at a concentration of from 5 µg/ml to 500 µg/ml, or from 10 µg/ml to 250 µg/ml, or from 10 µg/ml to 100 µg/ml and/or the linker molecule is immobilised in a line at the test site in an initial volume of from 50 nl/cm to 1 µl/cm, or from 100 nl/cm to 500 nl/cm, or from 150 nl/cm to 400 nl/cm. Alternatively, preferably, the linker molecule is provided at a concentration of from 5 µg/ml to 500 µg/ml, or from 10 µg/ml to 250 µg/ml, or from 10 µg/ml to 100 µg/ml and/or the linker molecule is immobilised in a line at the test site in an initial volume of from 500 nl/cm to 1 µl/cm, or from 700 nl/cm to 900 nl/cm, or from 750 nl/cm to 850 nl/cm. Preferably, when the linker molecule is a protein, and the first capture agent is morphine, the protein is provided at a concentration of from 10 µg/ml to 100 µg/ml, or from 10 µg/ml to 50 µg/ml, or from 20 µg/ml to 40 µg/ml and/or the protein is immobilised in a line at the test site in an initial volume of from 100 to 500 nl/cm. More preferably, the protein is immobilised in a line at the test site in an initial volume of from 150 to 400 nl/cm, or from 200 to 300 nl/cm, or from 225 nl/cm to 275 nl/cm. It is understood that the concentration of protein and the volume per cm at the test site will vary for other first capture reagents and depending on the required assay sensitivity and the number first capture reagents conjugated to each protein molecule.

Alternatively, preferably, when the linker molecule is a protein, and the first capture agent is morphine, the protein is provided at a concentration of from 10 µg/ml to 100 µg/ml, or from 10 µg/ml to 50 µg/ml, or from 20 µg/ml to 40 µg/ml and/or the protein is immobilised in a line at the test site in an initial volume of from 700 to 900 nl/cm, or from 750 nl/cm to 850 nl/cm.

Preferably, the device further comprises a control site, downstream of the test site, comprising a second immobilised capture reagent capable of binding to the labelled probe, the device being structured to permit movement of a buffer from the test site to the control site. As used herein, the term "second immobilised capture reagent" means that the second capture reagent is attached to or confined within the control site such that lateral flow of fluids across the control site during an assay will not dislodge the second capture reagent.

In use, as the buffer passes through the control site, the labelled probe dissolved therein will bind to the second immobilised capture reagent whether or not the labelled probe is bound to analyte from the sample. For example, when the sample comprises an antigen, and the labelled probe is a labelled antibody, the second immobilised capture reagent may comprise an immobilised antibody able to bind to the labelled antibody and any immunocomplex comprising the labelled antibody (the antibody-antigen complex). Accordingly, the control site as described herein is advantageous because it indicates that the assay has reliably worked. This is indicated by identifying the label, for example under appropriate radiation at the control site. Identifying the label at the control site after the assay is complete provides proof that the assay has reliably worked i.e. by confirming that the labelled probe has been dissolved by the buffer and has passed through the test site. If the label is not present at the control site after the assay is complete, the assay may not have reliably worked.

Preferably, the second immobilised capture reagent comprises an antibody or aptamer, more preferably an antibody, specific to the labelled probe. Preferably, the second immobilised capture reagent comprises an antibody, affimer or aptamer, more preferably an antibody, specific to the labelled probe. As used herein, when an antibody, affimer or aptamer is "specific" to the labelled probe, the antibody, affimer or aptamer binds to the labelled probe whether or not the labelled probe has binding sites available.

Preferably, the device further comprises a normalisation site, the normalisation site comprising an immobilised labelled protein incapable of binding to the labelled probe, the analyte, and any labelled probe-analyte complex, such as an immunocomplex, wherein the immobilised protein in the normalisation site and the probe are labelled with the same label. In effect, the immobilised labelled protein has no affinity for any molecule in the assay and is therefore a constant control against which all other readings in the same assay may be compared and quantitated, thereby making it possible to normalise the data. For example, the normalisation site normalises the data with regard to environmental factors which may differ between assays on different devices. For example, the effect of temperature on binding kinetics can be taken into account. Increased binding rates will be observed with increasing temperature until the proteins start to denature, at which point binding rates will decrease. In one embodiment, the device will monitor the assay temperature and will normalise data via look-up tables with reference to the constant fluorescent signal in the normalisation site. Furthermore, for example, when the probe and immobilised protein at the normalisation site are fluorescently labelled, environmental factors such as temperature-dependent quenching of the fluorophore can be taken into account.

Preferably, the device further comprises a sink downstream of the test site and/or the control site, the device being configured to permit movement of a buffer from the test site and/or the control site to the sink, wherein the sink is configured to prevent movement of the buffer from the sink. Preferably, the sink serves to "pull" any fluids/buffer added to the device for the duration of the assay by absorbing the fluids/buffer. Preferably, the sink is of sufficient capacity and absorption ability to ensure that fluids/buffer do not backflow upstream to the test site and/or control site, which may compromise the assay results. Preferably, the sink has a volume of from 100 to 500 μl. More preferably, the sink has a volume of from 100 to 400 μl, or from 100 to 300 μl, or from 100 to 250 μl, or from 100 to 200 μl. Alternatively, preferably, the sink has a volume of from 125 to 300 μl, or from 150 to 250 μl, or from 175 to 215 μl. Alternatively, preferably, the sink has a volume of from 150 to 550 μl, or from 200 to 500 μl, more preferably from 250 to 400 μl, or from 300 to 375 μl, most preferably from 325 to 350 μl. Preferably the sink comprises an absorbent and/or hydrophilic material. Preferably, the sink comprises one or more of high density cellulose, glass fibre/cellulose mix and cotton linter/fibres.

Preferably, the device further comprises a backing layer. Preferably, the backing layer serves as a physical support or a base upon which the sample receiving portion, the labelled probe zone, the test site, and optionally the control site and/or the normalisation site and/or the sink, are mounted. Preferably, the backing layer comprises a plastic strip such as, for example, polystyrene. The sample receiving portion, the labelled probe zone, the test site, and optionally the control site and/or the normalisation site and/or the sink may be mounted to the backing layer by an adhesive, preferably a hydrophobic adhesive. Preferably, the permeable membrane(s), backing layer and any adhesive do not scatter light or fluoresce at the wavelengths used to identify the one or more labels, thereby improving the reliability of the assay.

Preferably, the device further comprises a fingerprint pattern receiving zone, wherein the fingerprint pattern receiving zone is separate to the sample receiving zone. Preferably, the fingerprint pattern receiving zone comprises a different material to the sample receiving zone. Preferably, the fingerprint pattern receiving zone comprises glass and/or plastic and/or silicon wafer. The fingerprint pattern receiving zone is preferably provided so that the sample donor (which is preferably another fingerprint) can be positively identified before, during, or after the assay.

Preferably, the lateral flow device is housed within a cassette defining an aperture for receiving a sample on the sample receiving portion. Preferably, the aperture for receiving a sample is configured such that the sample is deposited onto a pre-determined area of the sample receiving portion. Preferably, the aperture is substantially oblong, substantially circular or substantially oval. Preferably, the pre-determined area of the sample receiving portion is 60 to 100% of the area of the fingerprint of an average adult human. More preferably, the pre-determined area of the sample receiving portion is 70 to 100%, or from 80 to 100%, or from 90 to 100%, of the area of the fingerprint of an average adult human. Such a configuration of the aperture provides more normalised results from sample to sample.

Preferably, the lateral flow device is housed within a cassette defining a window for viewing a test signal and/or a control signal and/or a normalisation signal. The window is positioned above the test site and/or the control site and/or the normalisation site, to permit visualisation or detection of the test site and/or the control site and/or the normalisation site. The window is preferably formed of a transparent polymer material. The results of the assay may be viewed through the window by eye, a detector, or reader system. Non-limiting examples of such devices include spectrophotometers, reflectance readers, luminometers, fluorometers, photodetectors or photomultiplier tubes, scintillation counters, photodiodes, photodiode arrays and charge-coupled devices.

In one embodiment, preferably, the lateral flow device is housed within a cassette defining an aperture for receiving a buffer upstream of the sample receiving portion.

Preferably, the present invention further provides a method for analysing a sample comprising from 0.1 pg to 1 μg of analyte, the method comprising:
  (a) providing a sample, the sample containing or not containing from 0.1 pg to 1 μg of an analyte of interest;
  (b) dissolving at least a portion of the sample in a buffer to form a dissolved sample solution;
  (c) contacting at least a portion of the dissolved sample solution with a probe zone comprising a labelled probe to dissolve at least a portion of the labelled probe and allow the labelled probe to bind with the analyte, where present, in the portion of the dissolved sample solution to form a labelled probe-analyte complex;
  (d) passing the labelled probe and/or labelled immunocomplex through a test site comprising a first immobilised capture reagent capable of binding to the labelled probe;
  (e) determining whether or not the amount of analyte, if any, in the sample exceeds a threshold value by detecting the amount of labelled probe in the test site.

The labelled probe-analyte complex, formed in step (c) if analyte is present in the sample, is understood to have no binding sites available to the first immobilised capture reagent. Therefore, the first immobilised capture reagent is capable of binding to the labelled probe, and incapable of binding to the labelled probe-analyte complex.

Preferably, the sample comprises sweat, preferably eccrine sweat. More preferably, the sample comprises finger-sweat and/or palm-sweat and/or toe-sweat. Most preferably, the sample comprises finger-sweat.

Preferably, the sample is provided in step (a) on a sample receiving portion of a lateral flow device, the device further comprising:
  the probe zone downstream of the sample receiving portion;
  the test site, downstream of the probe zone, comprising a first immobilised capture reagent capable of binding to the labelled probe;
  the device being configured to permit movement of a buffer from the sample receiving portion to the probe zone and from the probe zone to the test site.

Preferably, the sample is provided directly to the sample receiving portion, i.e. the sample is preferably not subjected to any process steps between obtaining the sample and providing the sample to the sample receiving portion. Preferably, the sample is not suspended in a buffer before being provided to the sample receiving portion.

Preferably, the sample provided in step (a) is substantially dry, such that the sample comprises insufficient liquid to move from the sample receiving zone to the probe zone, for example by capillary action.

Preferably, the sample is provided in step (a) as a fingerprint, the fingerprint comprising sweat deposited as an impression of a finger's ridge pattern.

Preferably, step (b) is carried out by providing the buffer upstream of the sample receiving portion and passing the buffer through the sample receiving portion.

Preferably, the sample is dissolved in step (b) such that the sample is contacted with the probe zone at the solvent front in step (c).

Preferably, the buffer is provided in a volume of from 100 to 500 µl. More preferably, the buffer is provided in a volume of from 100 to 450 µl, or from 100 to 400 µl, or from 100 to 350 µl, or from 100 to 300 µl, or from 100 to 250 µl, or from 100 to 200 µl. Alternatively, preferably, the buffer is provided in a volume of from 125 to 300 µl, or from 150 to 250 µl, or from 175 to 215 µl of buffer. Alternatively, preferably, the buffer is provided in a volume of from 150 to 550 µl, or from 200 to 500 µl, more preferably from 250 to 400 µl, or from 300 to 375 µl, most preferably from 325 to 350 µl. Larger volumes of buffer may be advantageous by helping to wash away any unbound labelled probe from the test site and/or the control site and prevent false readings.

Preferably, the buffer to sample volume ratio is from 50:1 to 1,000 to 1, more preferably from 100:1 to 1,000:1, or from 200:1 to 1,000:1, or from 300:1 to 1,000:1, or from 400:1 to 1,000:1. More preferably still, the buffer to sample volume ratio is from 500:1 to 1,000:1.

Preferably, the buffer composition is as described above in relation to the lateral flow device of the present invention.

Preferably, the sample comprises from 0.1 pg to 1 µg of analyte. More preferably, the sample comprises from 0.1 pg to 500 ng, or from 0.1 pg to 200 ng, or from 0.1 pg to 100 ng, or from 0.1 pg to 50 ng, or from 0.1 pg to 10 ng, or from 0.1 pg to 5 ng, or from 0.5 pg to 4 ng, or from 0.5 pg to 3 ng, or from 1 pg to 2 ng, or from 1 pg to 1 ng, or from 1 pg to 500 pg, or from 1 pg to 400 pg, or from 1 pg to 300 pg, or from 2 pg to 250 pg, or from 3 pg to 225 pg, or from 5 pg to 200 pg of analyte. Alternatively, the sample comprises from 10 pg to 2 ng, or from 20 pg to 1.5 ng, or from 30 pg to 1.25 ng, or from 40 pg to 1 ng, or from 50 pg to 500 pg, or from 50 pg to 300 pg, or from 50 pg to 200 pg of analyte.

Preferably, the analyte, if present, comprises a drug metabolite and/or a drug. Drugs that may be detected using the method of the present invention, if suitable antibodies are available, include, but are not limited to:

A. ANABOLIC AGENTS. These include, but are not limited to:

1. Anabolic Androgenic Steroids (AAS)

a. Exogenous* AAS, including:

1-androstendiol (5α-androst-1-ene-3β,17β-diol); 1-androstendione (5α-androst-1-ene-3,17-dione); bolandiol (19-norandrostenediol); bolasterone; boldenone; boldione (androsta-1,4-diene-3,17-dione); calusterone; clostebol; danazol (17α-ethynyl-17β-hydroxyandrost-4-eno[2,3-d]isoxazole); dehydrochlormethyltestosterone (4-chloro-17β-hydroxy-17α-methylandrosta-1,4-dien-3-one); desoxymethyltestosterone (17α-methyl-5α-androst-2-en-17β-ol); drostanolone; ethylestrenol (19-nor-17α-pregn-4-en-17-ol); fluoxymesterone; formebolone; furazabol (17β-hydroxy-17α-methyl-5α-androstano[2,3-c]-furazan); gestrinone; 4-hydroxytestosterone (4,17β-dihydroxyandrost-4-en-3-one); mestanolone; mesterolone; metenolone; methandienone (17β-hydroxy-17α-methylandrosta-1,4-dien-3-one); methandriol; methasterone (2α, 17α-dimethyl-5α-androstane-3-one-17β-ol); methyldienolone (17β-hydroxy-17α-methylestra-4,9-dien-3-one); methyl-1-testosterone (17β-hydroxy-17α-methyl-5α-androst-1-en-3-one); methylnortestosterone (17β-hydroxy-17α-methylestr-4-en-3-one); methyltrienolone (17β-hydroxy-17α-methylestra-4,9,11-trien-3-one); methyltestosterone; mibolerone; nandrolone; 19-norandrostenedione (estr-4-ene-3,17-dione); norboletone; norclostebol; norethandrolone; oxabolone; oxandrolone; oxymesterone; oxymetholone; prostanozol ([3,2-c]pyrazole-5α-etioallocholane-17β-tetrahydropyranol); quinbolone; stanozolol; stenbolone; 1-testosterone (17β-hydroxy-5α-androst-1-en-3-one); tetrahydrogestrinone (18a-homo-pregna-4,9,11-trien-17β-ol-3-one); trenbolone, and other substances with a similar chemical structure or similar biological effect(s).

b. Endogenous** AAS:

androstenediol (androst-5-ene-3β,17β-diol); androstenedione (androst-4-ene-3,17-dione); dihydrotestosterone (17β-hydroxy-5α-androstan-3-one); prasterone (dehydroepiandrosterone, DHEA); testosterone and the following metabolites and isomers:

5α-androstane-3α,17α-diol; 5α-androstane-3α,17β-diol; 5α-androstane-3β,17α-diol; 5α-androstane-3β,17β-diol; androst-4-ene-3α,17α-diol; androst-4-ene-3α,17β-diol; androst-4-ene-3β,17α-diol; androst-5-ene-3α,17α-diol; androst-5-ene-3α,17β-diol; androst-5-ene-3β,17α-diol; 4-androstenediol (androst-4-ene-3β,17β-diol); 5-androstenedione (androst-5-ene-3,17-dione); epi-dihydrotestosterone; 3α-hydroxy-5α-androstan-17-one; 3β-hydroxy-5α-androstan-17-one; 19-norandrosterone; 19-noretiocholanolone.

*"exogenous" refers to a substance which is not ordinarily capable of being produced by the body naturally.

**"endogenous" refers to a substance which is capable of being produced by the body naturally.

2. Other Anabolic Agents. These include, but are not limited to:

Clenbuterol, tibolone, zeranol, zilpaterol.

B. Hormones. These include, but are not limited to:

1. Erythropoietin (EPO);
2. Growth Hormone (hGH), Insulin-like Growth Factors (e.g. IGF-1), Mechano Growth Factors (MGFs);
3. Gonadotrophins (LH, hCG), prohibited in males only;
4. Insulin;
5. Corticotrophins.

C. BETA-2 AGONISTS, including their D- and L-isomers.

D. AGENTS WITH ANTI-ESTROGENIC ACTIVITY. These include, but are not limited to:

1. Aromatase inhibitors including, but not limited to, anastrozole, letrozole, aminoglutethimide, exemestane, formestane, testolactone.
2. Selective Estrogen Receptor Modulators (SERMs) including, but not limited to, raloxifene, tamoxifen, toremifene.
3. Other anti-estrogenic substances including, but not limited to, clomiphene, cyclofenil, fulvestrant.

E. DIURETICS AND OTHER MASKING AGENTS. These include, but are not limited to:

Diuretics*, epitestosterone, probenecid, alpha-reductase inhibitors (e.g. finasteride, dutasteride), plasma expanders (e.g. albumin, dextran, hydroxyethyl starch) and other substances with similar biological effect(s).

Diuretics include:

acetazolamide, amiloride, bumetanide, canrenone, chlorthalidone, etacrynic acid, furosemide, indapamide, metolazone, spironolactone, thiazides (e.g. bendroflumethiazide, chlorothiazide, hydrochlorothiazide), triamterene, and other substances with a similar chemical structure or similar biological effect(s).

F. AGENTS FOR THE ENHANCEMENT OF OXYGEN TRANSFER. These include, but are not limited to:

1. Autologous, homologous or heterologous blood or red blood cell products of any origin.
2. perfluorochemicals, efaproxiral (RSR13) and modified haemoglobin products (e.g. haemoglobin-based blood substitutes, microencapsulated haemoglobin products).

G. STIMULANTS (including both their (D- & L-) optical isomers where relevant). These include, but are not limited to:

Adrafinil, adrenaline, amfepramone, amiphenazole, amphetamine, amphetaminil, benzphetamine, benzylpiperazine, bromantan, cathine*, clobenzorex, cocaine, cropropamide, crotetamide, cyclazodone, dimethylamphetamine, ephedrine**, etamivan, etilamphetamine, etilefrine, famprofazone, fenbutrazate, fencamfamin, fencamine, fenetylline, fenfluramine, fenproporex, furfenorex, heptaminol, isometheptene, levmethamfetamine, meclofenoxate, mefenorex, mephentermine, mesocarb, methamphetamine (D-), methylenedioxyamphetamine, methylenedioxymethamphetamine, pmethylamphetamine, methylephedrine**, methylphenidate, modafinil, nikethamide, norfenefrine, norfenfluramine, octopamine, ortetamine, oxilofrine, parahydroxyamphetamine, pemoline, pentetrazol, phendimetrazine, phenmetrazine, phenpromethamine, phentermine, 4-phenylpiracetam (carphedon), prolintane, propylhexedrine, selegiline, sibutramine, strychnine, tuaminoheptane and other substances with a similar chemical structure or similar biological effect(s).

H. NARCOTICS These include, but are not limited to:

Buprenorphine, dextromoramide, diamorphine (heroin), fentanyl and its derivatives, hydromorphone, methadone, morphine, codeine, oxycodone, oxymorphone, pentazocine, pethidine.

I. CANNABINOIDS These include, but are not limited to:

Hashish, marijuana.

J. GLUCOCORTICOSTEROIDS

K. ALCOHOL (ethanol).

L. BETA-BLOCKERS These include, but are not limited to:

acebutolol, alprenolol, atenolol, betaxolol, bisoprolol, bunolol, carteolol, carvedilol, celiprolol, esmolol, labetalol, levobunolol, metipranolol, metoprolol, nadolol, oxprenolol, pindolol, propranolol, sotalol, timolol.

M. AMPHETAMINES. These include, but are not limited to:

methamphetamine and MDMA (3,4-methylenedioxy-N-methylamphetamine); LSD (lysergic acid diethylamide); PCP (Phencyclidine), ketamine and derivatives;

N. ALKALOIDS AND THEIR DERIVATIVES. These include, but are not limited to:

nicotine, cocaine, ephedrine, mescaline; opium alkaloids (opiods), including morphine and codeine, and semi-synthetic opoids such as diamorphine (heroin); tryptamine alkaloids such as dimethyltriptamine and alpha-methyltryptamine;

O. BENZODIAZEPINES. These include, but are not limited to:

Alprazolam, Diazepam, Lorazepam, Clonazepam, Temazepam, Oxazepam, Flunitrazepam, Triazolam, Chlordiazepoxide, Flurazepam, and Nitrazepam, and nonbenzodiazepines, including Imidazopyridines, Pyrazolopyrimidines, Cyclopyrrones.

P. GHB (gamma-Hydroxybutyric acid) and derivatives.

The method and device of the present invention may be used to detect metabolites of the drugs mentioned above, for which antibodies are available. If an antibody for a particular target substance, such as a drug or its metabolite, is not available commercially, the person skilled in the art could readily raise such an antibody using known techniques.

Preferably, the analyte is one or more of morphine, cocaine, cannabis, benzodiazepine, amphetamine, methadone, buprenorphine and/or metabolites of one or more thereof. More preferably, the analyte is one or more of morphine, cocaine, and metabolites of one or more thereof.

Alternatively, preferably, the analyte is one or more of morphine, cocaine, cannabis, benzodiazepine, amphetamine, methadone, buprenorphine, codeine, dihydrocodeine, 6-methylacetyl morphine (6-MAM), alcohol and/or metabolites of one or more thereof, including metabolites of cocaine such as benzoylecgonine, cocaethylene, ecgonine ethyl ester, ecgonine methyl ester and norcocaine, and metabolites of alcohol such as ethylglucuronide. More preferably, the analyte is one or more of morphine, cocaine, codeine, alcohol and metabolites of one or more thereof.

Preferably, the analyte is cocaine. Alternatively, preferably, the analyte is morphine. Alternatively, preferably, the analyte is cannabis. Alternatively, preferably, the analyte is amphetamine. Alternatively, preferably, the analyte is methamphetamine. Alternatively, preferably, the analyte is benzodiazepine. Alternatively, preferably, the analyte is methadone.

Alternatively, preferably, the analyte metabolite is a cocaine metabolite, selected from one or more of benzoylecgonine, cocaethylene, ecgonine ethyl ester, ecgonine methyl ester and norcocaine. More preferably, the analyte is benzoylecgonine.

Alternatively, preferably, the analyte metabolite is an alcohol metabolite. More preferably, the analyte metabolite is ethylglucuronide.

Preferably, the method further comprises:

(f) passing the labelled probe and/or the labelled probe-analyte complex through a control site comprising a second immobilised capture reagent capable of binding to the labelled probe and to the labelled probe-analyte complex; and (g) determining whether or not the test result is reliable by detecting or not detecting the labelled probe and/or the labelled probe-analyte complex in the control site.

Preferably, the labelled probe is detectable in radiation having a wavelength of 400 nm to 1 mm, and step (e) and/or step (g) is carried out by illuminating the test site and/or the first control site with radiation having a wavelength of 400 nm to 1 mm to show the labelled probe and/or labelled probe-analyte complex, if present.

Preferably, the method further comprises:

(h) illuminating a normalisation site with radiation having a wavelength of 400 nm to 1 mm, measuring the signal intensity of the normalisation site and comparing said signal intensity to the signal intensity detected at the test site and/or the control site;

wherein the normalisation site comprises an immobilised labelled protein incapable of binding to the labelled probe, the analyte, and any labelled probe-analyte complex comprising the labelled probe and the analyte; and wherein the immobilised labelled protein and the labelled probe are labelled with the same label.

Preferably, the method further comprises obtaining a fingerprint pattern on a fingerprint pattern receiving zone, wherein the fingerprint pattern receiving zone is separate to the sample receiving portion but is housed within the same device. Preferably, the method further comprises scanning and/or recording the fingerprint pattern.

The method is fast, accurate and inexpensive due to the reduced volume of sample and reagents (i.e. nanolitres/microlitres), inexpensive and disposable materials, and minimal testing steps. Fluid flow manipulation is governed by capillary action through the test strip. Fluid handling, separation and detection functionalities are conveniently integrated within the method. Samples may thus be processed rapidly in minutes, compared to current time-consuming technologies, for example, liquid chromatography-tandem mass spectrometry, radio-immunoassays, solvent extraction and HPLC, which require a high degree of proficiency, extensive training and expensive equipment. The device and method therefore reduces costs for both the patient and e.g. healthcare systems because the results may be obtained within minutes of performing the test, either at home or at a point-of-care location. Preferably, the method is carried out in from one to ten minutes.

Preferably, the present invention provides a method of preparing the lateral flow device as described herein, comprising:

providing a fingerprint receiving portion to a permeable membrane;

applying a labelled probe to the permeable membrane to create a probe zone;

applying to the permeable membrane and immobilising thereon a first capture reagent capable of binding to the labelled probe to create a test site.

The lateral flow device may be fabricated using techniques known to those skilled in the art. The labelled probe zone is pre-treated with labelled probe by dispensing or dipping, followed by drying. The first and optionally second capture reagents at the test and control sites can be immobilised using several methods well known to those skilled in the art including, for example, direct adsorption and covalent attachment. Blocking of non-specific binding may be achieved by coating the surface of the device, for example the permeable membrane, with blocking buffers such as for example, bovine serum albumin and/or detergent, followed by drying. The sample receiving portion may also be pre-treated to filter out particulates, bind sample components which might interfere with the assay, or disrupt the sample to release the target analyte. The device may be optionally be assembled on cards, with the sample receiving portion, the labelled probe zone, the test site, and optionally the control site and/or the normalisation site and/or the sink, being mounted onto a backing layer using an appropriate adhesive. The cards may then be cut into individual devices or strips.

Preferably, the method further comprises providing a buffer receiving portion to the permeable membrane and optionally a reservoir of buffer to the substrate.

Preferably, the method further comprises applying to the permeable membrane and immobilising thereon a second capture reagent capable of binding to the labelled probe to create a control site.

Preferably, the method further comprises applying to the permeable membrane and immobilising thereon a labelled protein to create a normalisation site, wherein the labelled protein is incapable of binding to the labelled probe.

Preferably, 10 pg to 1 µg of labelled probe is applied to the permeable membrane to create the probe zone. More preferably, from 10 pg to 500 ng, or from 10 pg to 400 ng, or from 10 pg to 300 ng, or from 10 pg to 250 ng, or from 10 pg to 200 ng, or from 10 pg to 100 ng, or from 10 pg to 1 ng, or from 10 pg to 500 pg, or from 10 pg to 200 pg, of labelled probe is applied to the permeable membrane to create the probe zone. Alternatively, preferably, from 50 pg to 500 ng, or from 200 pg to 400 ng, or from 500 pg to 300 ng, or from 1 ng to 250 ng, or from 10 ng to 200 ng, or from 20 ng to 150 ng, or from 30 ng to 100 ng, is applied to the permeable membrane to create the probe zone.

Preferably, the present invention provides a kit for the analysis of a sample, comprising:

the device as described herein; and a fluorescence, ultraviolet, infrared and/or a far infrared detector.

Preferably, the present invention provides a method of dissolving at least a portion of a bodily fluid, the method comprising contacting a bodily fluid with a buffer, the buffer comprising:

a water miscible organic solvent;

a surfactant, preferably a detergent; and a buffering agent.

It is advantageous that the buffer comprises all of the three components mentioned above. The buffer is effective at solubilising at least a portion of a bodily fluid such that the portion of bodily fluid can then be analysed using one or more reagents or techniques. The buffer's individual components and preferred amounts thereof are described in further detail below.

Water miscible solvents are known in the art. Preferably, the water miscible organic solvent comprises one or more of ethanol, methanol and tetrahydrofuran. Preferably, the buffer comprises 10 to 30 v/v % water miscible organic solvent. More preferably, the buffer comprises from 15 to 25 v/v %, or from 18 to 22 v/v % water miscible organic solvent. The water miscible organic solvent helps hydrophilic and hydrophobic molecules partition in water.

Surfactants are known in the art and may include any molecule that forms micelles, for example amphiphilic molecules. Preferably, the surfactant comprises one or more of TWEEN-20, TWEEN 80, TRITON X-100, tetraoctyl ammonium bromide, Polyethylene glycol (PEG) and octanoic acid. Alternatively, preferably, the surfactant comprises one or more of TWEEN-20, Tween 80, TRITON X-100, TRITON X-114, tetraoctyl ammonium bromide, Polyethylene glycol (PEG) and octanoic acid. More preferably, the surfactant comprises one or more of TWEEN-20, TWEEN 80, TRITON X-100 and tetraoctyl ammonium bromide. Alternatively, more preferably, the surfactant comprises one or more of TWEEN-20, TWEEN 80, TRITON X-100, TRITON X-114 and tetraoctyl ammonium bromide. Preferably, the buffer comprises 0.1 to 0.15 w/v % surfactant. More preferably, the buffer comprises 0.11 to 0.14 w/v %, or 0.12 to 0.13 w/v % surfactant. The surfactant, preferably a detergent, is thought to aid release of analyte, e.g. drugs and/or drug metabolites, from the bodily fluid. The surfactant molecules are preferably present in a concentration above their critical micelle concentration (CMC). The micelles thus present within the surfactant are preferably able to act as a carrier for any hydrophobic analyte, e.g. drugs and drug metabolites, and allow presentation of said analyte during analysis undertaken on the bodily fluid.

Suitable buffering agents are known in the art. Preferably, the buffering agent comprises one or more of HEPES, Tris, TRIZMA and phosphate buffer. Preferably, the buffer comprises 5 to 100 mM buffering agent. More preferably, the buffer comprises 5 to 75 mM, or 5 to 50 mM, or 5 to 25 mM, or 5 to 15 mM, or 5 to 10 mM, or 6 to 9 mM, or 7 to 8 mM buffering agent. The buffering agent is thought to assist in increasing the solubility of any analyte in the bodily fluid, e.g. drugs and/or drug metabolites, based on their pKa and PI values.

Preferably, the buffer further comprises one or more anti-oxidants. Suitable anti-oxidants include ethyl acetate, methyl anthranilate, 2-pentyl butyrate and ethyl butyrate. Anti-oxidants may help to prevent the oxidation of any analyte or metabolite thereof and any organic material in the bodily fluid, such as fingerprint lipids. This is desirable because, if the analyte and/or metabolite thereof is oxidised, its properties (e.g. its charge) may change. Any changes in physical or chemical properties could interfere with analysis of the analytes or metabolites Preferably, the buffer further comprises an emulsifier. Preferably, the emulsifier is selected from deoxycholate, cholesterol and combinations thereof. More preferably, the emulsifier is deoxycholate. Without wishing to be bound by theory, an emulsifier such as deoxycholate helps to present any analyte or metabolites thereof in the bodily fluid during analysis. This is thought to be achieved by the emulsifier helping to 'open up' any lipid structures in the sample encourage any hydrophobic analyte or metabolite to be available for binding.

In one embodiment, the buffer further comprises a salt. Preferably, the salt is selected from NaCl, KCl or a mixture thereof.

Preferably, the bodily fluid comprises finger-sweat.

Preferably, the present invention provides a lateral flow device for detecting from 0.1 pg to 1 µg of analyte in a sample.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

These and other aspects of the invention will now be described with reference to the accompanying Figures, in which:

FIG. 1: is a diagram of the lateral flow device according to one embodiment of the present invention.

Figure 2:
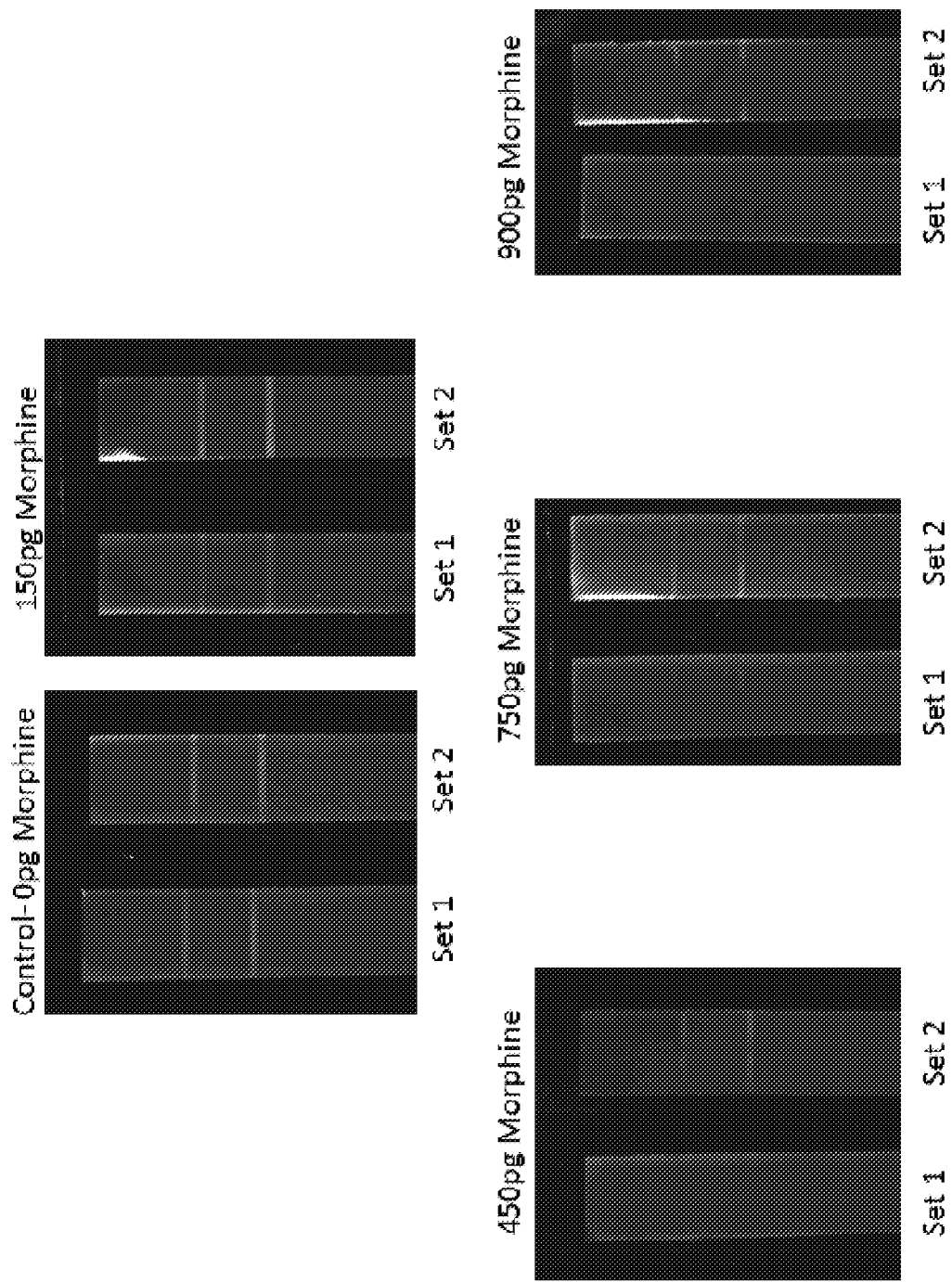
Figure 3:
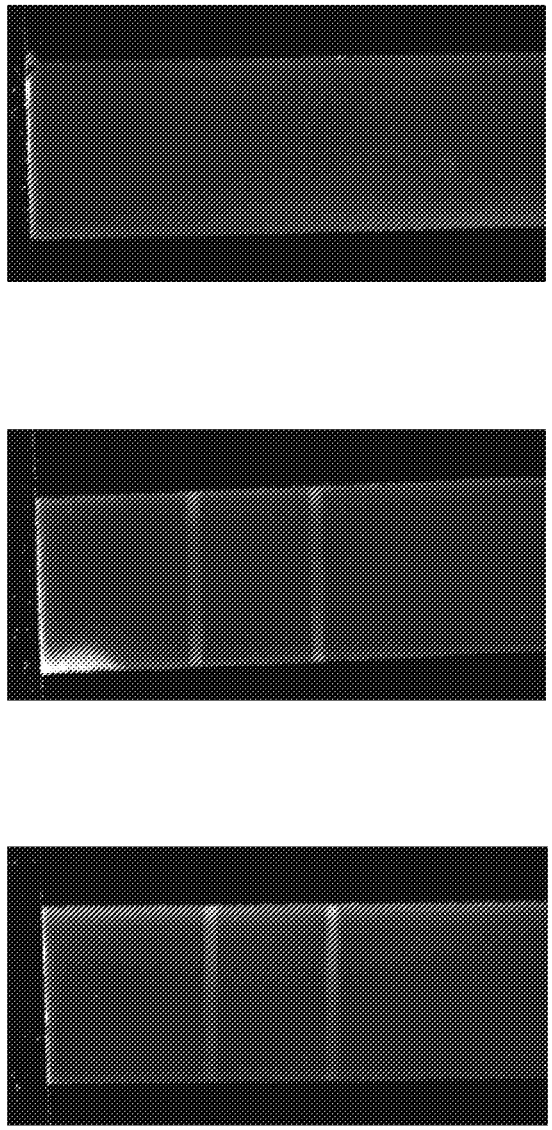
Figure 4:
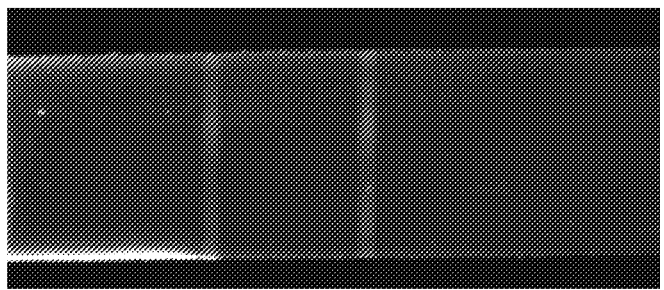
Figure 4:
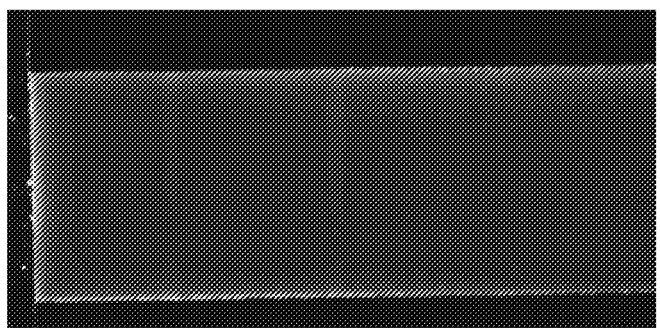
Figure 4:
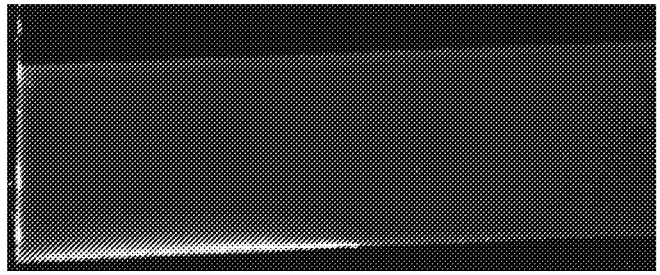
Figure 5:
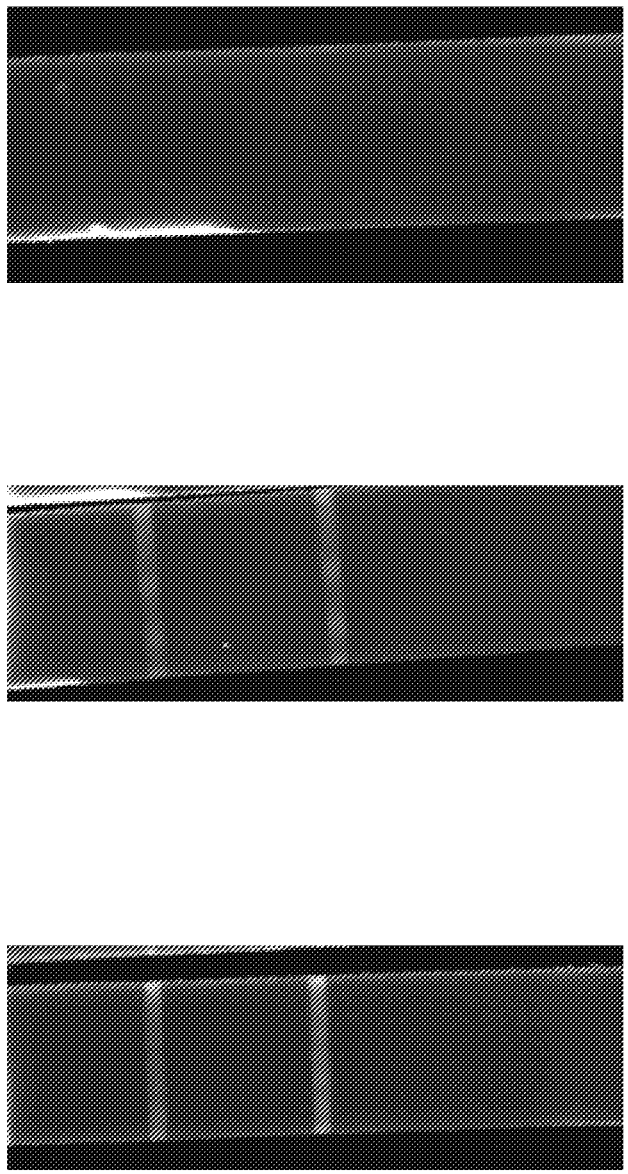
Figure 6:
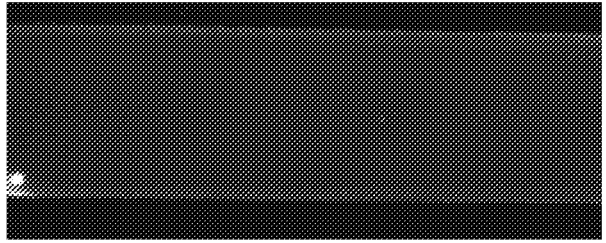
Figure 6:
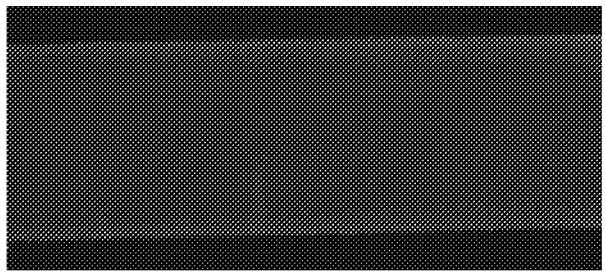
Figure 6:
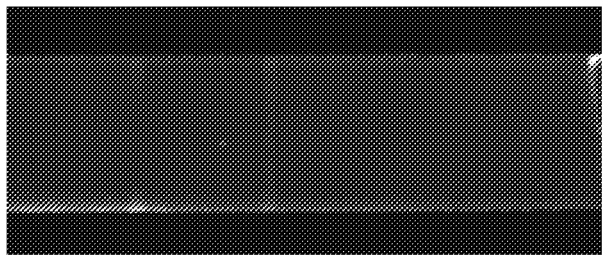
Figure 7:
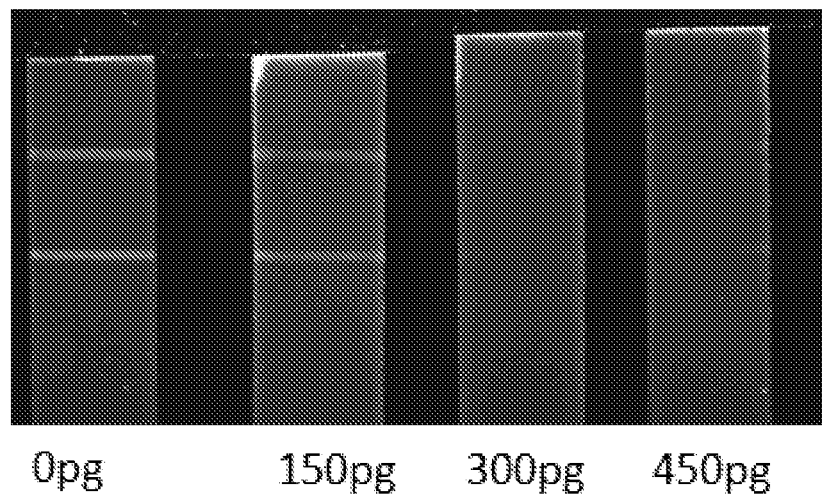
Figure 8:
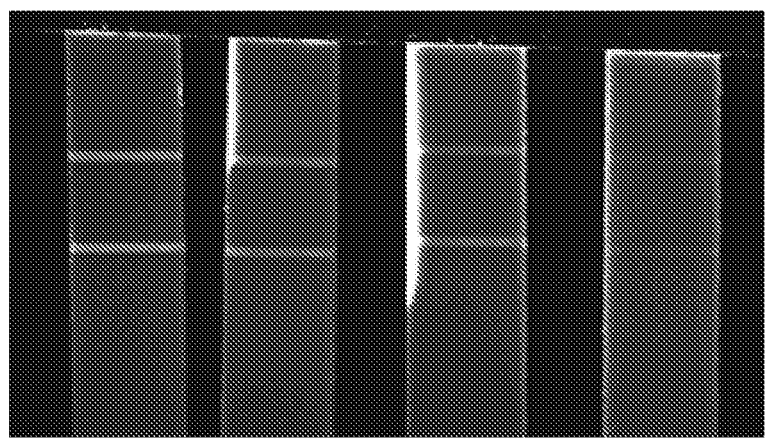
Figure 9:
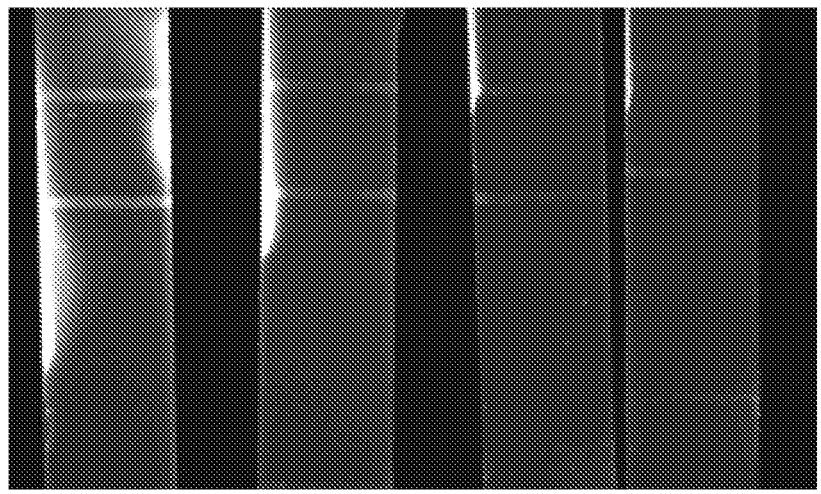
Figure 10:
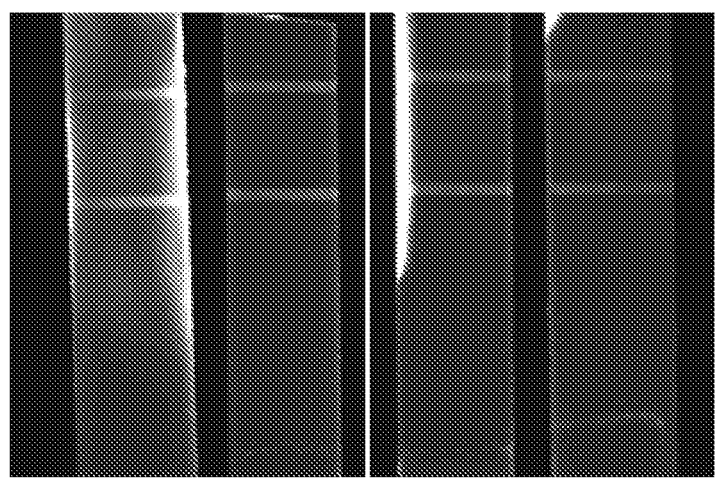

FIG. 2: is a photograph of lateral flow test strips obtained as set out in Example 1.

FIGS. 3 to 6: are images of lateral flow test strips obtained as set out in Example 2.

FIGS. 7 to 10: are images of lateral flow test strips obtained as set out in Example 3.

Figure 11:
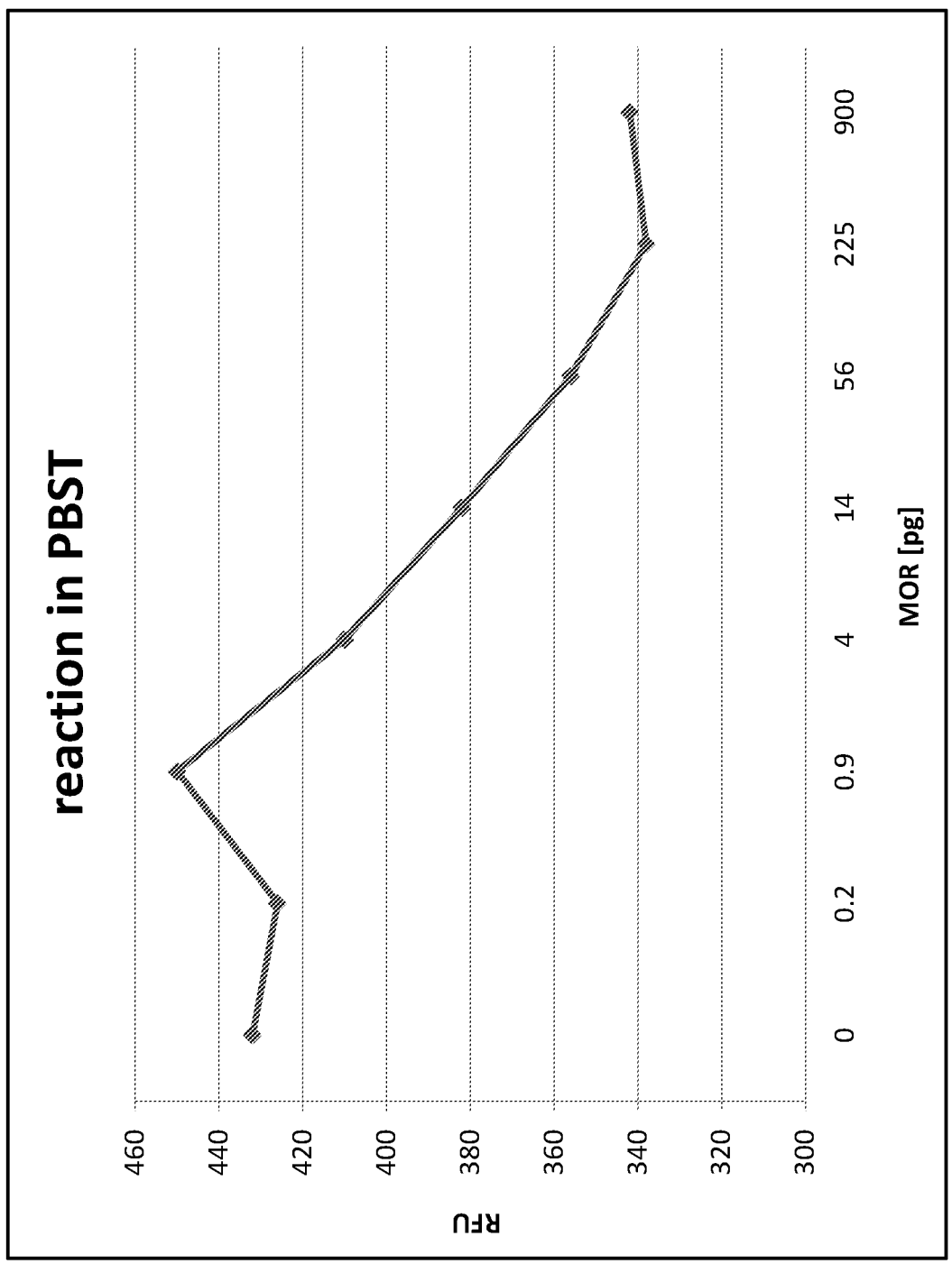

FIG. 11: is a graph showing the results of a comparison between a nitrocellulose lateral flow assay vs. plate assay.

Figure 12:
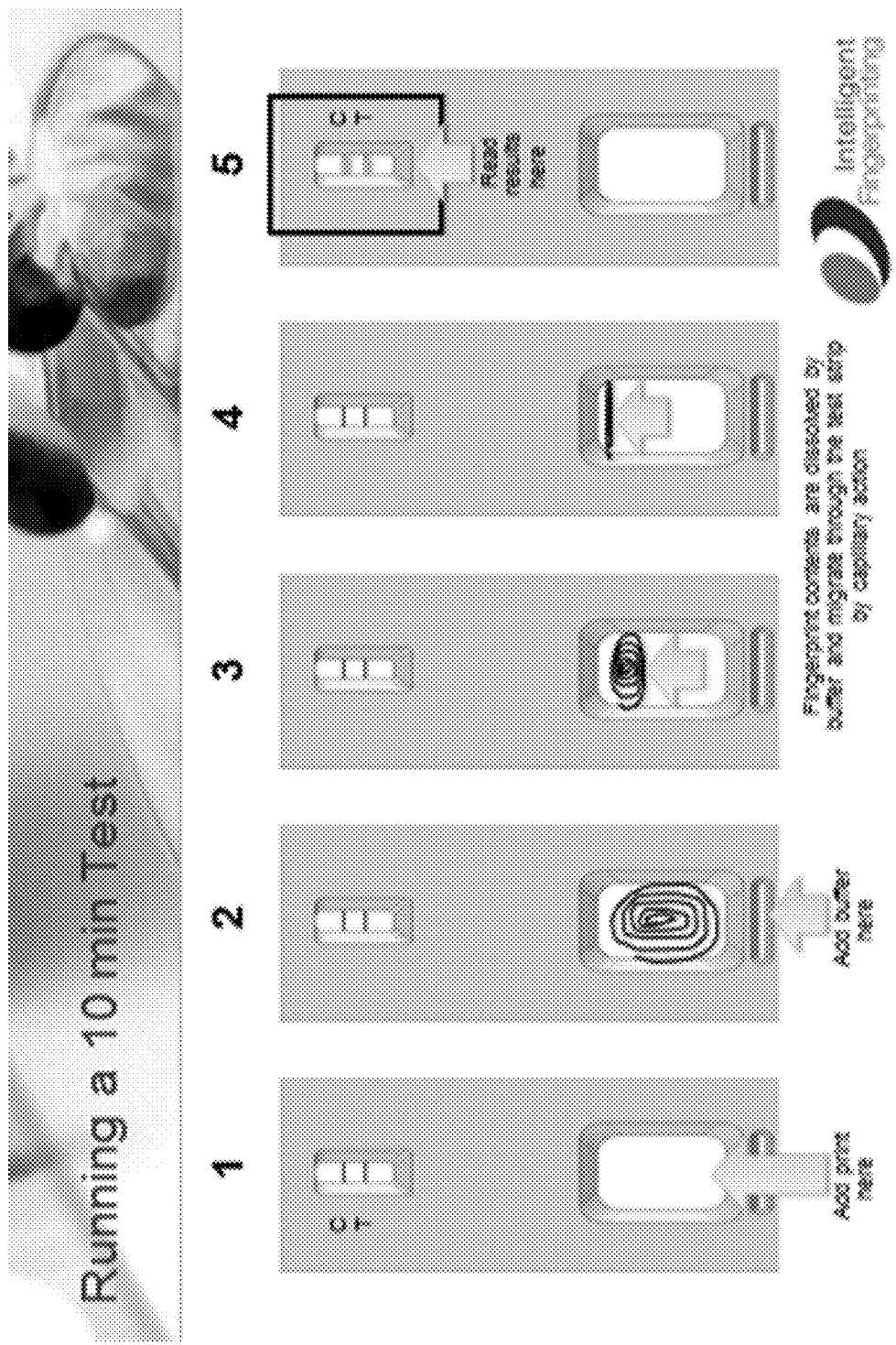

FIG. 12: is a diagram showing the steps of a ten minute assay using the device of the present invention.

Figure 13:
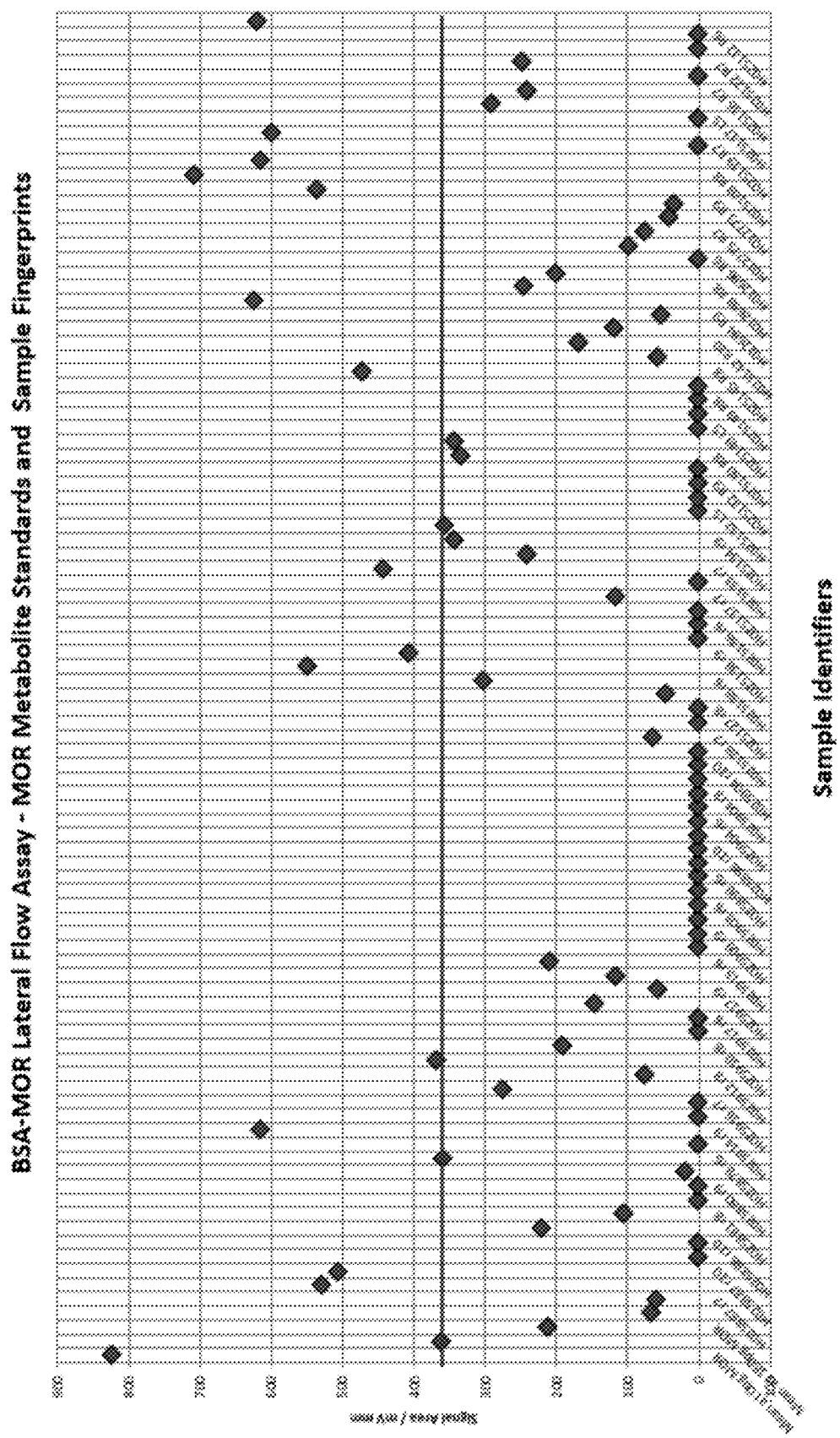

FIG. 13: is a graph showing results of the lateral flow tests on fingerprint samples taken from people testing positive for morphine by oral fluid analysis.

Figure 14:
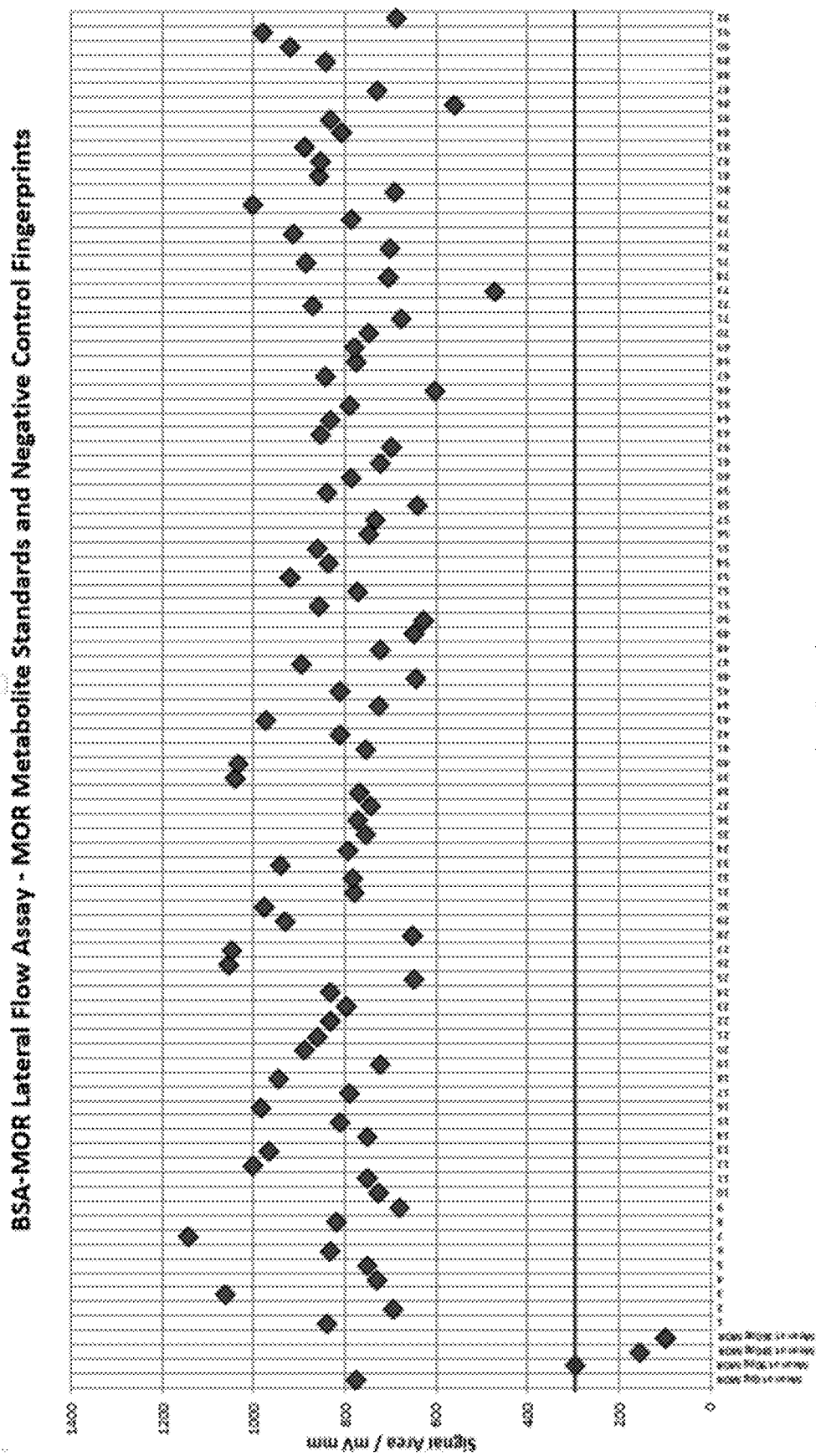

FIG. 14: is a graph showing results of the lateral flow tests on fingerprint samples taken from people testing negative for morphine by oral fluid analysis.

Figure 15:
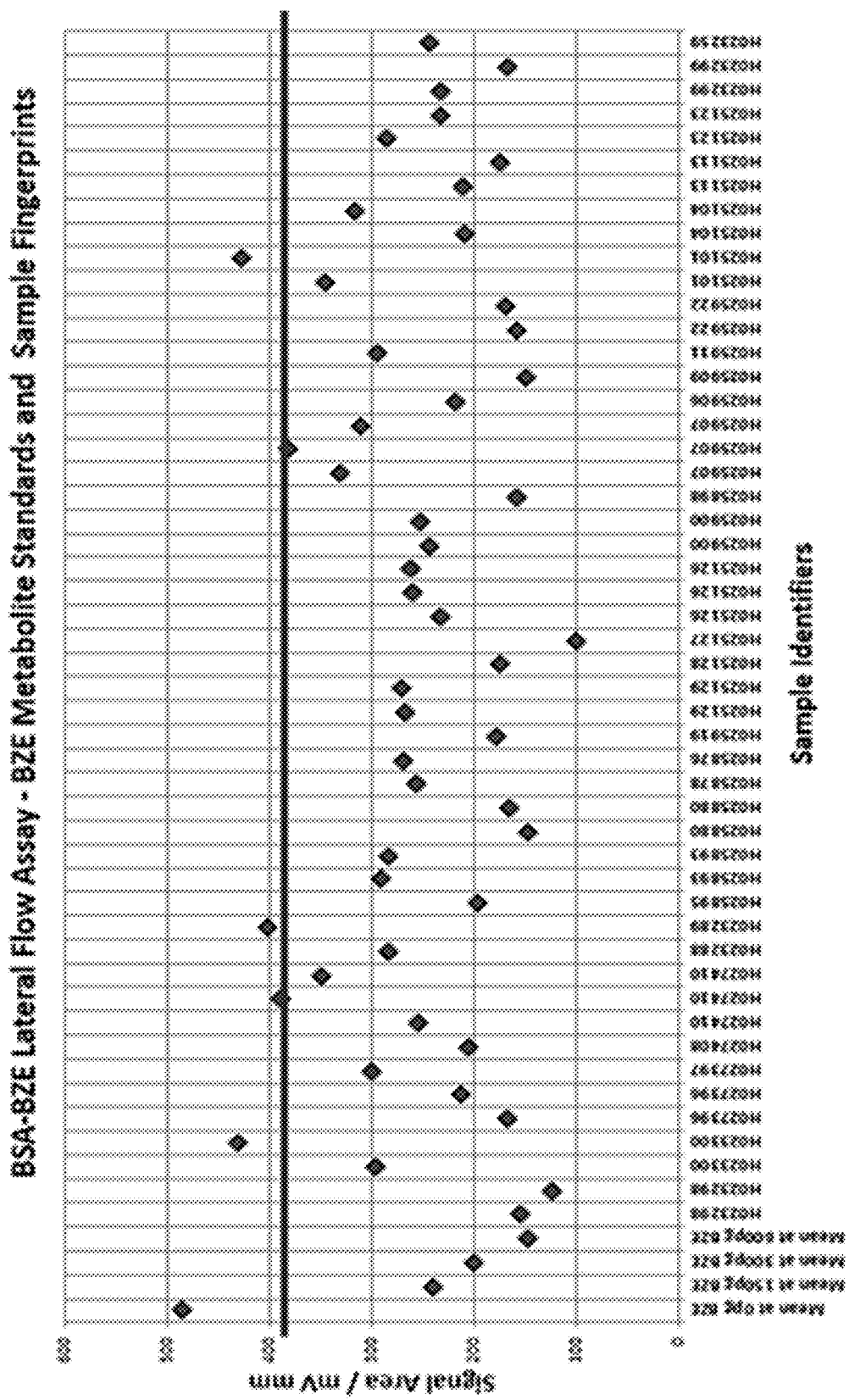

FIG. 15: is a graph showing results of the lateral flow tests on fingerprint samples taken from people testing positive for BZE by oral fluid analysis.

Figure 16:
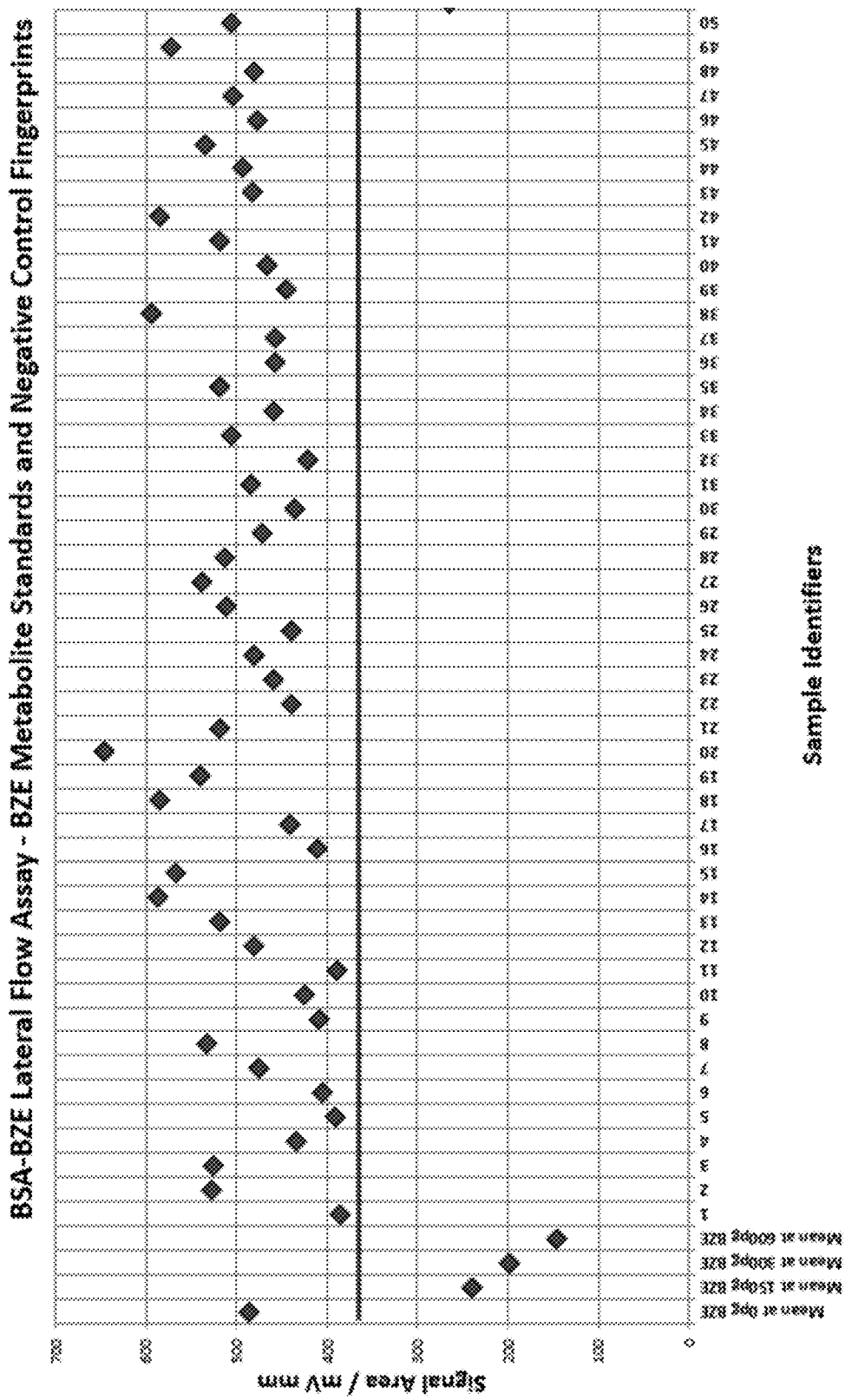

FIG. 16: is a graph showing results of the lateral flow tests on fingerprint samples taken from people testing negative for BZE by oral fluid analysis.

The following non-limiting examples further illustrate the present invention.

EXAMPLES

The present invention will now be described in relation to several examples.

Example 1: Homogeneously Distributed Dried Drug Over the Sample Receiving Portion is Concentrated at the Solvent Front when Solvent is Applied Upstream of the Deposited Sample Solution set 1 (Set 1): Morphine was dissolved in methanol at 0 to 900 pg per 100 µl of solvent.

Solution set 2 (Set 2): Morphine was dissolved in fingerprint solubilisation buffer at 0 to 900 pg per 100 µl of solvent.

A series of lateral flow strips of the present invention were set up having two test sites and no control sites. The volume of the sample receiving portion is around 110 µl.

Each test line (each test site) is BSA-Morphine (40 µg/ml) conjugate applied at 0.25 µl/cm.

The labelled probe zone is provided with 50 ng labelled antibody/zone in loading buffer (100 mM Sucrose in 10 mM PB pH 7.42, 1% (w/v) Tween-80).

100 µl of solution from Set 1 were applied to the sample receiving portion of a series of lateral flow strips and then dried.

100 µl of solutions from Set 2 were applied to the sample receiving portion of a second series of lateral flow strips and while still wet, fresh fingerprint solubilisation buffer was used to chase the liquid through the lateral flow strip by applying the buffer to the bottom edge of the pad i.e. upstream of the sample receiving portion. A similar application of fingerprint solubilisation buffer to the pads containing dried Morphine was performed in parallel.

Set 2 represents what would happen if solvent were applied directly to the fingerprint, similar to sample application
to sample pad areas of conventional test strips. Set 1 shows what happens when buffer is applied upstream of the print. Here buffer slowly wets the fingerprint area, solubilising the drug/drug metabolites as it advances downstream the lateral flow strip, incrementally concentrating the drug material at the buffer solvent front.

The assay results are shown in FIG. 2. The data clearly demonstrates that the drug in the membranes from Set 1 has been concentrated with respect to similar levels found in Set 2.

The method used by set 2 (similar to a typical lateral flow approach) is not sensitive enough and is unable to detect the lowest levels of drug found on the fingerprint which would indicate a person is just above the legal cut-off. The present invention clearly detects the drug/metabolite at 150 pg per sample.

Testing using the set 2 format only appears to detect the presence of drug/metabolite between 750 to 900 pg which is well above the cut-off and of no use for routine testing, as the value is too high.

Example 2

Fingerprints were collected from three patients on a variety of sample receiving portion materials on lateral flow strips of the present invention having two test sites and no control sites.

The saliva opiate levels of the patients were confirmed by LGC as follows:
Donor 04745007: Negative
Donor 04745008: >1700 ng/ml of opiates—Very high levels
Donor 04745009: >10 ng/ml of 6-acetyl morphine (opiate heroin marker)—level 2.5× Cut-off value Lateral flow assays were run by applying the solubilisation buffer of Example 1. Images of the resulting test lines were captured by illumination of the samples for 5 seconds each.

The results are shown in FIGS. 3 to 6.

For each of the four substrates tested, clear inhibition (opiate detection) is seen for sample 04745008. Partial inhibition is observed for sample 04745009 which is in line with low levels of metabolite. Use of a calibration curve would allow quantitation of this value.

The results show that the sample receiving portion may comprise any material that does not bind the analyte (drug or drug metabolite) being investigated and allows buffer to migrate through it slowly in order to collect and concentrate the metabolite at the solvent front.

Example 3: Evidence for Varying the Assay Sensitivity Range

Samples having 0 pg, 150 pg, 300 pg and 450 pg of morphine were provided on sample receiving portion of lateral flow strips of the present invention having two test sites and no control sites.

Assays were run, varying the amount of labelled antibody and/or amount of antigen in the test sites.

FIGS. 7 to 10 show the results obtained.

Cut-off values for opiates may be around 90 pg per print. Similar studies have been done for the cocaine metabolite BZE, the cut-off value for which is around 68 pg per print.

The results show that the lower the amount of antibody, the more sensitive the assay is, which is useful for detecting low levels of drugs and/or drug metabolites. Also, the lower the amount of immobilised antigen in the test sites, the more sensitive the assay is.

Example 4: Comparison Between a Nitrocellulose Lateral Flow Assay Vs. Plate Assay A Plate was coated with 50 μg/ml BSA-MOR (4.7 mg/ml): at 4° C., overnight:
5.3 μl stock+495 μl 100 mM bicarbonate buffer pH 9.5 (diluted from 1077RD)

After incubation, the coated wells were washed 3× with 100 μl PBST (from 1402RD, diluted to 1× with H2O)

A series of dilution of MOR was prepared:
Stock solutions: 1 mg/ml
Stock was diluted to 10 μg/ml: 10 μl stock+990 μl PBST (from 1402RD, diluted to 1× with H2O) The 10 μg/ml solution was further diluted to 100 ng/ml: 10 μl 10 μg/ml+990 μl PBST (from 1402RD, diluted to 1× with H2O)

A 4-fold dilution series was prepared starting with 100 ng/ml:
25 ng/ml: 50 μl 100 ng/ml+150 μl PBST (from 1402RD, diluted to 1× with H2O)
6.25 ng/ml: 50 μl 100 ng/ml+150 μl PBST (from 1402RD, diluted to 1× with H2O)
1.56 ng/ml: 50 μl 100 ng/ml+150 μl PBST (from 1402RD, diluted to 1× with H2O)
0.39 ng/ml: 50 μl 100 ng/ml+150 μl PBST (from 1402RD, diluted to 1× with H2O)
0.09 ng/ml: 50 μl 100 ng/ml+150 μl PBST (from 1402RD, diluted to 1× with H2O)
0.02 ng/ml: 50 μl 100 ng/ml+150 μl PBST (from 1402RD, diluted to 1× with H2O)
0.006 ng/ml: 50 μl 100 ng/ml+150 μl PBST (from 1402RD, diluted to 1× with H2O)
0.0015 ng/ml: 50 μl 100 ng/ml+150 μl PBST (from 1402RD, diluted to 1× with H2O)
0.0004 ng/ml: 50 μl 100 ng/ml+150 μl PBST (from 1402RD, diluted to 1× with H2O)
0.0001 ng/ml: 50 μl 100 ng/ml+150 μl PBST (from 1402RD, diluted to 1× with H2O)
Control: PBST (from 1402RD, diluted to 1× with H2O)

rabbit anti-MOR-FITC antibody dilution was prepared:
1 μl stock (mAbF-MOR-004-006; 0.5 mg/ml)+99 μl extraction buffer 1420RD or PBST (from 1402RD, diluted to 1× with H2O)

18 μl of MOR dilution was incubated with 2 μl of rabbit anti-MOR-FITC and incubated at room temp. for 4 min 10 μl from these reactions were transferred into the BSA-MOR coated wells and incubated for 4 min at room temperature After incubation, the wells were washed 3× with 100 μl PBST (from 1402RD, diluted to 1× with H2O)

empty wells were filled with 10 μl PBST (1402RD) and the fluorescence was measured in a plate reader with a 485 nm excitation filter and a 535 nm emission filter for 1 s experiment with PBST as solvent: concentration-dependent inhibition; sensitivity: approx. 0.1-0.39 ng/ml The results are shown in FIG. 11, a dose response curve which shows the detection of morphine in the 4 pg-225 pg range.

Example 5

Oral fluid was taken from 184 people and the fluid analysed for the presence of morphine and/or metabolites thereof. Positive samples were shown to comprise morphine and/or metabolites thereof. Negative samples were shown to not comprise morphine and/or metabolites thereof. There were 92 positive samples and 92 negative samples Fingerprint samples were taken from the same people and the lateral flow device as described herein was used to test for the presence of morphine or metabolites thereof. The cut-off point for detecting the presence of morphine in the fingerprint was 180 pg, i.e. the fingerprint samples shown to comprise 180 pg or more of morphine and/or metabolites thereof were deemed positives, whilst the samples shown to comprise less than 180 pg or more of morphine and/or metabolites thereof were deemed negatives.

The results were compared to the results obtained via oral fluid analysis. A test showing the presence of morphine and/or metabolites thereof which agreed with the oral fluid analysis was deemed to be a true positive (TP). A test showing the presence of morphine and/or metabolites thereof which did not agree with the oral fluid analysis was deemed to be a false positive (FP). A test not showing the presence of morphine and/or metabolites thereof which agreed with the oral fluid analysis was deemed to be a true negative (TN). A test not showing the presence of morphine and/or metabolites thereof which did not agree with the oral fluid analysis was deemed to be a false negative (FN).

The results of the tests done on the fingerprint samples taken from the people who had tested positive by oral fluid analysis are shown in FIG. 13. The results above the horizontal cut off line are false negatives. The results below the horizontal cut off line are true positives.

The results of the tests done on the fingerprint samples taken from the people who had tested negative by oral fluid analysis are shown in FIG. 14. The results above the horizontal cut off line are true negatives. The results below the horizontal cut off line are false positives.

The percentage accuracy, percentage sensitivity and percentage specificity of the lateral flow test for morphine and/or metabolites thereof can thus be calculated as follows:

Accuracy=((Total number of TP+Total number of TN)/Total number of samples)×100

Sensitivity=(Total number of TP/(Total number of TP+Total number of FN))×100

Specificity=(Total number of TN/(Total number of TN+Total number of FP))×100

The results showed that the accuracy of the lateral flow test, which can detect whether a sample has more or less than 180 pg of morphine, was 92.9%. The sensitivity was 85.9%. The specificity was 100%.

Example 6

Example 6 is identical to Example 5 with the exception that the drug metabolite tested was benzoylecgonine (BZE) (the major metabolite of cocaine), there were 100 people's samples taken (50 positive and 50 negative), and the cut-off point for the fingerprint samples was 150 pg of BZE, i.e. the fingerprint samples shown to comprise 150 pg or more of BZE were deemed positives whilst the fingerprint samples shown to comprise less than 150 pg of BZE were deemed negatives.

The results of the tests done on the fingerprint samples taken from the people who had tested positive by oral fluid analysis are shown in FIG. 15. The results above the horizontal cut off line are false negatives. The results below the horizontal cut off line are true positives.

The results of the tests done on the fingerprint samples taken from the people who had tested negative by oral fluid analysis are shown in FIG. 16. The results above the horizontal cut off line are true negatives. The results below the horizontal cut off line are false positives.

The results showed that the accuracy of the lateral flow test, which can detect whether a fingerprint sample has more or less than 150 pg BZE, was 95%. The sensitivity was 90%. The specificity was 100%.

The invention claimed is:

1. A method for analysing a sample comprising from 0.1 pg to 1 µg of analyte, the method comprising:
    (a) directly contacting a region of a subject's skin comprising a ridge pattern with a sample receiving portion of a lateral flow device to provide a sample on the sample receiving portion, the lateral flow device comprising a permeable membrane including the sample receiving portion, a probe zone and a test site, the lateral flow device being housed within a cassette, and the sample receiving portion being aligned with an aperture of the cassette that is sized to receive a fingerprint of the subject, the sample containing or not containing from 0.1 pg to 1 µg of an analyte of interest, wherein the sample comprises finger-sweat and/or toe-sweat;
    (b) passing a buffer through the sample to form a dissolved sample solution in which any analyte is concentrated therein;
    (c) contacting at least a portion of the dissolved sample solution with the probe zone comprising a labelled probe to dissolve at least a portion of the labelled probe and allow the labelled probe to bind with the analyte, where present, in the portion of the dissolved sample solution to form a labelled probe-analyte complex;
    (d) passing the labelled probe and/or labelled probe-analyte complex through the test site comprising a first immobilised capture reagent capable of binding to the labelled probe;
    (e) determining whether or not the amount of analyte, if any, in the sample exceeds a threshold value by detecting the amount of labelled probe in the test site;
    wherein the lateral flow device further comprises:
    the probe zone downstream of the sample receiving portion; and
    the test site, downstream of the probe zone and aligned with a window of the cassette;
    the device being configured to permit movement of the buffer from the sample receiving portion to the probe zone and from the probe zone to the test site; and
    wherein step (b) is carried out by providing the buffer upstream of the sample receiving portion and passing the buffer through the sample receiving portion,
    wherein the sample provided in step (a) is substantially dry, such that the sample comprises insufficient liquid to move from the sample receiving zone to the probe zone, and
    wherein the buffer comprises a water miscible organic solvent, a surfactant, a buffering agent, and an emulsifier.

2. The method of claim 1, wherein the sample comprises finger-sweat.

3. The method of claim 1, wherein the sample is provided in step (a) as a fingerprint, the finger sweat and/or toe sweat being deposited as an impression of a finger's ridge pattern.

4. The method of claim 1, wherein the buffer is provided in a volume of from 100 to 500 µl.

5. The method of claim 1, wherein the buffer to sample volume ratio is from 50:1 to 1,000 to 1.

6. The method of claim 1, wherein the sample comprises from 0.1 pg to 5 ng of analyte.

7. The method of claim 1, wherein the probe zone comprises from 10 pg to 1,000 ng of labelled probe.

8. The method of claim 1, wherein the probe is selected from the group consisting of an antibody, an aptamer, an affimer, and mixtures thereof.

9. The method of claim 1, wherein the first immobilised capture reagent comprises an antigen capable of binding to the labelled probe.

10. The method of claim 1, wherein the first immobilised capture reagent comprises two or more different antigens capable of binding to the labelled probe.

11. The method of claim 1, wherein the analyte, if present, comprises a drug metabolite and/or a drug.

12. The method of claim 1, further comprising:
(f) passing the labelled probe and/or the labelled probe-analyte complex through a control site comprising a second immobilised capture reagent capable of binding to the labelled probe and to the labelled probe-analyte complex; and
(g) determining whether or not the test result is reliable by detecting or not detecting the labelled probe and/or the labelled probe-analyte complex in the control site.

13. The method of claim 1, wherein the labelled probe is detectable in radiation having a wavelength of 400 nm to 1 mm, and wherein step (e) is carried out by illuminating the test site with radiation having a wavelength of 400 nm to 1 mm to show the labelled probe and/or labelled probe-analyte complex, if present.

14. The method of claim 1, further comprising:
(h) illuminating a normalisation site with radiation having a wavelength of 400 nm to 1 mm, measuring the signal intensity of the normalisation site and comparing said signal intensity to the signal intensity detected at the test site and/or the control site;
wherein the normalisation site comprises an immobilised labelled protein incapable of binding to the labelled probe, the analyte, and any labelled probe-analyte complex comprising the labelled probe and the analyte; and
wherein the immobilised labelled protein and the labelled probe are labelled with the same label.

15. The method of claim 1, further comprising obtaining a fingerprint pattern on a fingerprint pattern receiving zone, wherein the fingerprint pattern receiving zone is separate to the sample receiving portion but is housed within the same device.

16. The method of claim 15, further comprising scanning and/or recording the fingerprint pattern.

17. The method of claim 1, wherein the buffer is provided in a blister reservoir.

18. The method of claim 1, wherein the permeable membrane has a length in a lateral flow direction and a width perpendicular to the lateral flow direction, the width of the permeable membrane of the lateral flow device at the sample receiving portion being greater than the width at the probe zone.

19. The method of claim 1, wherein the surfactant is a detergent.

* * * * *